(12) United States Patent
Matulic-Adamic et al.

(10) Patent No.: US 6,586,238 B1
(45) Date of Patent: *Jul. 1, 2003

(54) ENZYMATIC NUCLEIC ACIDS CONTAINING 5'-AND OR 3'-CAP STRUCTURES

(75) Inventors: Jasenka Matulic-Adamic, Boulder, CO (US); Leonid Beigelman, Longmont, CO (US); Alexander Karpeisky, Boulder, CO (US); Thale Jarvis, Boulder, CO (US); Nassim Usman, Boulder, CO (US); Anthony DiRenzo, Boulder, CO (US); Francine Wincott, Longmont, CO (US)

(73) Assignee: Ribozyme Pharmaceuticals, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/419,125

(22) Filed: Oct. 15, 1999

Related U.S. Application Data

(63) Continuation of application No. 08/632,882, filed on Apr. 16, 1996, now Pat. No. 5,998,203.

(51) Int. Cl.$^7$ .............................. C07H 21/04; C12N 5/00
(52) U.S. Cl. ..................... 435/325; 536/23.1; 536/23.2; 536/24.5
(58) Field of Search .................. 435/6, 91.31, 366, 435/325, 375; 514/44; 536/23.1, 23.2, 24.3, 24.5, 25.3

(56) References Cited

U.S. PATENT DOCUMENTS

| | | | |
|---|---|---|---|
| 4,987,071 A | | 1/1991 | Cech et al. |
| 5,256,775 A | * | 10/1993 | Froehler ................... 536/25.6 |
| 5,270,185 A | * | 12/1993 | Magolskee ............... 435/91.41 |
| 5,334,711 A | | 8/1994 | Sproat et al. |
| 5,476,925 A | * | 12/1995 | Letsinger et al. .......... 536/23.1 |
| 5,583,032 A | * | 12/1996 | Torrence et al. ......... 435/240.2 |
| 5,623,065 A | * | 4/1997 | Cook et al. ................ 536/23.1 |
| 5,629,147 A | * | 5/1997 | Asgari et al. ................... 435/5 |
| 5,646,042 A | * | 7/1997 | Stinchcomb ............... 435/366 |
| 5,672,511 A | * | 9/1997 | Beigelman et al. ......... 435/325 |
| 5,891,683 A | * | 4/1999 | Usman et al. ........... 435/91.31 |
| 5,998,203 A | * | 12/1999 | Matulic-Adamic et al. . 435/325 |
| 6,117,657 A | * | 9/2000 | Usman et al. ........... 435/91.31 |
| 6,251,666 B1 | * | 6/2001 | Beigelman .................. 435/325 |

FOREIGN PATENT DOCUMENTS

| | | |
|---|---|---|
| CA | WO2106819 | 3/1994 |
| EP | 0 360 257 | 3/1990 |
| WO | WO-89/05358 A1 * | 6/1989 |
| WO | WO9207065 | 4/1992 |
| WO | WO9315187 | 8/1993 |
| WO | WO9402595 | 2/1994 |

OTHER PUBLICATIONS

Agrofoglio et al., "Synthesis of Carbocyclic Nucleosides," Tetrahedron 1994, 50, 10611.

Atkinson, T., Smith, M. in *Oligonucleotide Synthesis: A Practical Approach*, Gail, M.J., Ed IRL Press Oxford, 1984, pp 35–81.

Azad et al., "Antiviral Activity of a Phosphorothioate Oligonucleotide Complementary to RNA of the Human Cytomegalovirus Major Immediate–Early Region," Antimicrobial Agents and Chemotherapy 37:1945–1954 (1993).

Bannwarth, "Solid–Phase Synthesis of Oligodeoxynucleotides Containing Phosphoramidate Internucleotide Linkages and their Specific Chemical Cleavage," *Helv. Chim. Acta* 1988, 71, 1517–1527.

Beaucage and Iyer, "The Functionalization of Oligonucleotides Via Phosphoramidite Derivatives," *Tetrahedron* 49:1925–1963 (1993).

Beigelman et al., "Chemical Modification of Hammerhead Ribozymes," *J. Biol. Chem.* 270:25702–25708 (1995).

Bock et al., "Selection of election of single–stranded DNA molecules that bind and inhibit human thrombin," *Nature* 355:564–566 (1992).

Cech, "Ribozymes and Their Medical Implications," *JAMA* 260:3030–3034 (1988).

Chen et al., "Synthesis of Oligodeoxyribonucleotide N3'>P5' Phosphoramidates," *Nucleic Acids Res.* 1995, 23, 2661–2668.

Chladek and Nagyvary, "Nucleophilic Reactions of Some Nucleoside Phosphorothioates," *Journal of the American Chemical Society* 94:2079–2085 (1972).

Christoffersen and Marr, "Riobozymes as Human Therapeutic Agents," *J. Med. Chem.* 38:2023–2037 (1995) (also referred to as Christofferson and Marr).

Cook, "Nucleoside S–Alkyl Phosphorothioates IV. Synthesis of Nucleoside Phosphorothioate Monoesters," *Amer. Chem. Soc.*, 1970, 92, 190–195.

Cosstick and Vyle "Solid Phase Synthesis of Oligonucleotides Containing 3'–Thiothymidine," *Tetrahedron Lett.* 1989, 30, 4693–4696.

Cosstick et al, "Synthesis and properties of dithymidine phosphate analogues containing 3'–thiothymidine," *Nucleic Acids. Research* 18:829–835 (1990).

De Clercq et al., "The Antiviral Activity of Thiophosphate–Substituted Polyribonucleotides in Vitro and in Vivo," *Virology* 42:421–428 (1970).

Debart et al., "Synthesis and Base–pairing Properties of the Nucleas–resistant α–anomeric Dodecaribonucleotide α–[r(UCUUAACCCACA)]," 1992, *Nucleic Acid Res.* 20, 1193.

(List continued on next page.)

Primary Examiner—Sean McGarry
Assistant Examiner—Janet Epps-Ford
(74) Attorney, Agent, or Firm—McDonnell Boehnen Hulbert & Berghoff

(57) ABSTRACT

An enzymatic nucleic acid molecule comprising a 5'- and/or a 3'-cap structure, wherein said structure is not a 5'-5'-linked inverted nucleotide or a 3'-3'-linked inverted nucleotide.

20 Claims, 15 Drawing Sheets

OTHER PUBLICATIONS

Debart et al., "Sugar Modified Oligonucleotides: II. Solid Phase Synthesis of Nuclease Resistant α–Anomeric Uridylates as Potential Antisense Agents" 1995, *Tetrahedron Lett.* 31, 3537.

Forster and Altman, "External Guide Sequences for an RNA Enzyme," *Science* 249:783–786 (1990).

Gao et al., "Phosphorothioate Oligonucleotides Are Inhibitors of Human DNA Polymerases and Rnase H: Implications for Antisense Technology," *Molecular Pharmacology* 41:223–229 (1992).

Gryaznov and Letsinger, "Synthesis and properties of oligonucleotides containing aminodeoxythymidine units," *Nucleic Acids Research* 20:3403–3409 (1992).

Gryaznov and Sokolova, "A New Method for the Synthesis of Oligodeoxyribonucleotides Containing Internucleotide Phosphoramidate Bonds," *Tetrahedron Lett.* 1990, 31, 3205–3208.

Guerrier–Takada et al., "The RNA Moiety of Ribonuclease P Is the Catalytic Subunit of the Enzyme," *Cell* 35:849–857 (1983).

Guo and Collins, "Efficent *trans*–cleavage of a stem–loop RNA substrate by a ribozyme derived from *Neurospora* VS RNA," *EMBO J.* 14:368–376 (1995).

Hampel and Tritz, "RNA Catalytic Properties of the Minimum (–)sTRSV Sequence," *Biochemistry* 28:4929–4933 (1989).

Hampel et al., "'Hairpin' Catalytic RNA Model: Evidence for Helices and Sequence Requirement for Substrate RNA," *Nucleic Acids Research* 18:299–304 (1990).

Haseloff and Gerlach, "Simple RNA Enzymes with New and Highly Specific Endoribonuclease Activities," *Nature* 334:585–591 (1988).

Heidenreich et al., "Chemically Modified RNA: Approaches and Applicantions," 1993 *FASEB J.* 7, 90.

Inoue et al., "Synthesis and hybridization studies on two complementary nona(2'–O–methyl) ribonucleotides," *Nucleic Acids Research* 15:6131–6149 (1987).

Jeffries and Symons, "A Catalytic 13–mer Ribozyme," *Nucleic Acids Research* 17:1371–1377 (1989) (also referred to as Jefferies).

Kamber, "Die Synthese von Insulinfragmenten mit intakter interchenarere Disulfidbrücke $A^{20}$–$B^{19}$," *Hlev. Chim. Acta* 1971, 54, 398–422.

Kim and Cech, "Three–dimensional model of the active site of the self–splicing rRNA precursor of *Tetrahymena*," *Proc. Natl. Acad. Sci. USA* 84:8788–8792 (1987).

Letsinger and Mungall, "Phosphoramidate Analogs of Oligonucleotides," *J. Org. Chem.* 35:3800–3803 (1970).

Li et al., "Application of the Michaelis–Arbusov Reaction to the Synthesis of Internucleoside 3'–S–Phosphorothiolate Linkages," *J. Chem. Soc. Perkin Trans.* I 15:2123–2129 (1994).

Li et al., "Synthesis of a Dinucleoside 3'–S–Phosphorothiolate Containing 2'–Deoxy–3'–Thioadenosine," *Tetrahedron* 48:2729–2738 (1992).

Limbach et al., "Summary: the modified nucleosides of RNA," *Nucleic Acids Research* 22(12):2183–2196 (1994).

Liu and Reese, "Uridylyl–(3'→ 5'–thiouridine). An Exceptionally Base–labile Di–ribonucleoside Phosphate Analogue," *Tetrahedron Lett.* 1995, 36, 3413–3416.

Liu et al., "3'–Thiouridylyl–(3'→ 5')–uridine," *Tetrahedron Letters* 37:925–928 (1996).

Lyngstadaas et al., "A synthetic, chemically modified ribozyme eliminates amelogenin, the major translation product in developing mouse enamel in vivo," *EMBO J.* 14:5224–5229 (1995).

Mag and Engels, "Synthesis and Selective Cleavage of Oligodeoxyribonucleotides Containing Non–2hiral Internucleotide Phosphoramidate Linkages," *Nucleic Acids Research* 17:5973–5989 (1989).

Mag and Engels, "Phosphoramidate Analogs of Dinucleotides: Synthesis and $^1$H Assignment by Two Dimensional NMR Spectroscopy ($^1$H, $^1$H–COSY)," *Nucleosides & Nucleotides* 1988, 7, 725–728.

Mag and Engels, "Synthesis of Dinucleotides Containing a Bridged Non–Chiral Internucleotide 5' – or 3'– Phosphoramidate Linkage," *Tetrahedron* 1994, 50, 10225–10234.

Mag et al., "Synthesis and Selective Cleavage of an Oligodeoxynucleotide Contatining a Bridged Non–Chiral Internucleotide 3'–Phosphoramidate Linkage," *Tetrahedron Lett.* 1992, 33, 7319–7322.

Marti et al., "Oligodeoxyribonucleotide Phosphorothioate Fluxes and Localization in Hematopoietic Cells," *Antisense Research and Development* 2:27–39 (1992).

Moffatt, "Chemical Transformations of the Sugar Moiety of Nucleosides," in *Nucleoside Analogues: Chemistry*, Biology and Medical Applications, Walker et al. eds., Plenum Press, New York, pp. 71–164 (1979).

Mungall et al., "Use of the Azido Group in the Synthesis of 5' Terminal Aminodeoxythymidine Oligonucleotides," *J. Org. Chem.* 40:1659–1662 (1975).

Perez et al., "Sequence–independent induction of Sp1 transcription factor activity by phosphorothioate oligodeoxynucleotides," *Proc. Natl Acad Sci. U.S.A.* 91:5957–5961 (1994).

Perreault et al., "Mixed Deoxyribo– and Ribo–Oligonucleotides with Catalytic Activity," *Nature* 344:565–567 (1990) (often mistakenly listed as Perrault).

Perrotta and Been, "A pseudoknot–like structure required for efficeint self–cleavage of hepatitis delta virus RNA," *Nature* 350:434–436 (1991).

Pieken et al., "Kinetic Characterization of Ribonuclease–Resistant 2'–Modified Hammerhead Ribozymes," *Science* 253:314–317 (1991).

Pyng–Shaw et al., "Modified deoxyoligonucleotides stable to exonuclease degradation in serum," *Nucleic Acids Research* 19:747–750 (1991).

Rossi et al., "Ribozymes as Anti–HIV–1 Therapeutic Agents: Principles, Applications, and Problems," *Aids Research and Human Retroviruses* 8:183–189 (1992).

Saville and Collins, "A Site–Specific Self–Cleavage Reaction Performed by a Novel RNA In Neurospora Mitochondria," *Cell* 61:685–696 (1990).

Saville and Collins, "RNA–Mediated Ligation of Self–Cleavage Products of a *Neurospora* Mitochondrial Plasmid Transcript," *Proc. Natl. Acad. Sci. USA* 88:8826–8830 (1991).

Scaringe et al., "Chemical synthesis of biologically active oligoribonucleotides using β–cyanoethyl protected ribonucleoside phosphoramidites," *Nucl Acids Res.* 18:5433–5441 (1990).

Seliger et al., "New Developments in the Field of Antisense Oligonucleotides," *Progress in Biotechnology 9* ECB6: Proceedings of the 6$^{th}$ European Congress on Biotechnology, Florence, Italy, Jun. 13–17, 1993 (Pt. 2) (Elsevier, 1994).

Sproat et al., "The synthesis of protected 5'–mercapto–2', 5'–dideoxyribonucleoside–3'–O–phosphoramidites; uses of 5'–mercapto–oligodeoxyribonucleotides," Nucleic Acids Research 15:4837–4848 (1987).

Sund and Chattopadhyaya, "Intra– and Intermolecular Nucleophilic Phosphorus—Sulfur Bond Cleavage. The reaction of Fluoride Ion with O–Aryl–O,S—Dialkylphosphorothioates, & the Degradation of Phosphorothioate Linkage in di–Ribonucleotides by the Vicinal 2'–Hydroxyl Group," *Tetrahedron* 1989, 45, 7523–7544.

Szekeres et al., "Synthesis and Study of Certain d–Erythrofuranosyl Nucleosides," 1972, *J. Carbohydr. Nucleosides Nucleotides*, 4, 147.

Uhlenbeck, "A Small Catalytic Oligoribonucleotide," *Nature* 328:596–600 (1987) (this is listed as Nature 327 in the various specifications, but it is actually 328).

Uhlmann and Peyman, "Antisense Oligonucleotides: A New Therapeutic Principle," *Chemical Reviews* 90:544–584 (1990).

Usman and Cedergren, "Exploiting the chemical synthesis of RNA," *TIBS* 17:334–339 (1992).

Usman and McSwiggen, "Ch. 30—Catalytic RNA (Ribozymes) as Drugs," *Annual Reports in Medicinal Chemistry* 30:285–294 (1995).

Usman et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethoionine tRNA," J. Am. Chem. Soc. 109:7845–7854 (1987).

Verheyden and Moffat, "Halo Sugar Nucleosides. I. Iodination of the Primary Hydroxyl Groups of Nucleosides with Methyltriphenoxyphosphonium Iodide[1],"*J. Org. Chem.* 1970, 35, 2319–2326.

Vyle et al., "Sequence– and Strand–Specific Cleavage in Oligodeoxyribonucleotides and DNA Containing 3'–Thiothymidine," Biochemistry 31:3012–3018 (1992).

Wincott et al., "Synthesis, deprotection, analysis and purification of RNA and ribozymes," *Nucleic Acids Research* 23(14):2677–2684 (1995).

Yamamoto et al., *J. Chem. Soc. Perkin I* 1978, 306–310.

Zaug et al., "The *Tetrahymena* Ribozyme Acts Like an RNA Restriction Endonuclease," *Nature* 324:429–433 (1986).

Zielinski and Orgel, *Nucleic Acids Res.* 1987, 15, 1699–1715.

* cited by examiner

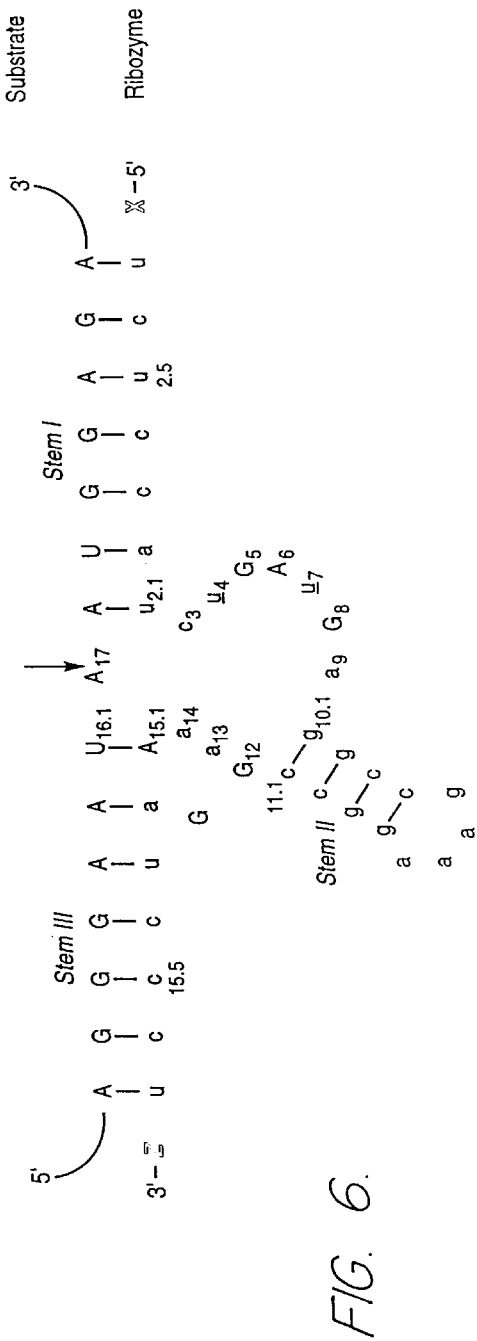

FIG. 6.

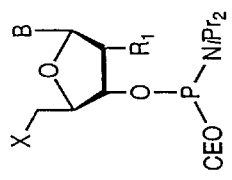

X = H, alkyl, MMTrNH-alkyl, DMTO-alkyl, Hal, CHal$_3$, NHMMTr, NHR, NR$_2$, NO$_2$, CONH$_2$, COOR, STr, SR-alkyl, OR, N$_3$, ONHR, or ONR$_2$
B = Natural bases, Modified bases or H
R$_1$ = H, O-Alkyl, C-Alkyl, TBDMSi, Hal, NHR (R = protecting group), or OCH$_2$SCH$_3$ 5'-modified sugars synthesis: Moffat, J.G. In *Nucleoside Analogues: Chemistry, Biology and Medical Applications*, Walker, R.T. De Clercq E., Eckstein, F., Eds.: Plenum Press: New York, 1979, pp 71.

FIG. 7A.

z = O or S
y = O, S or NHR$_1$ (R$_1$ = alkyl or H)
R = H, 2'-O-Alkyl, 2'-C-Alkyl, Hal, NHR$_1$ (R$_1$ = H, alkyl, aryl, acyl), or O-CH$_2$SCH$_3$
B = natural bases, modified bases or H X = OH, Y = NH, Z = O
X = NH$_2$, Y = O, Z = O
X = OH, Y = S, Z = O
X = OH, Y = O, Z = S R = H, 2'-O-Alkyl, O-Si, 2'-C-Alkyl, Hal, NHR$_1$ (R$_1$ = H, alkyl, aryl, acyl), or O-CH$_2$SCH$_3$
B = natural bases, modified bases or H

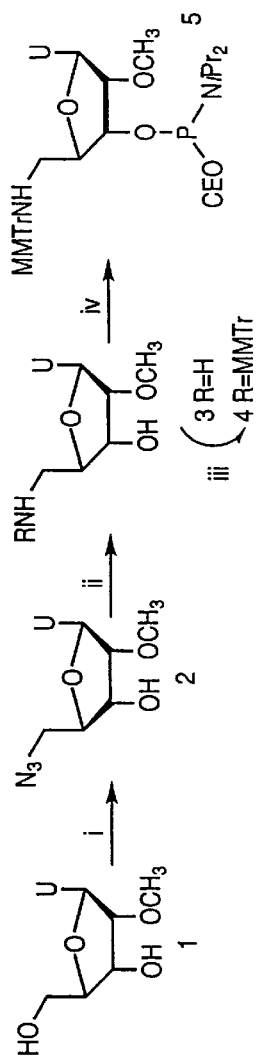
FIG. 8B.
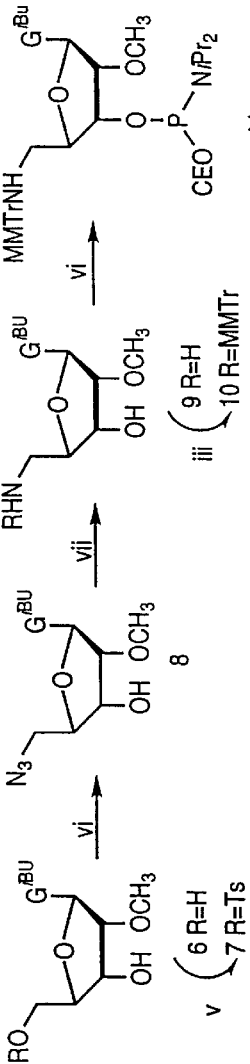
Reagents:
i, Ph₃P/CBr₄/LiN₃/DMF; ii, Ph₃P/Pyr/NH₄OH; iii, MMTr-Cl/DMAP/Et₃N/Pyr; iv, P(OCE)(NiPr₂)Cl/DIPEA/CH₂Cl₂; v, Ts-Cl/Pyr; vi, LiN₃/DMF/55 °C; vii, 10% H₂/Pd-C/EtOH
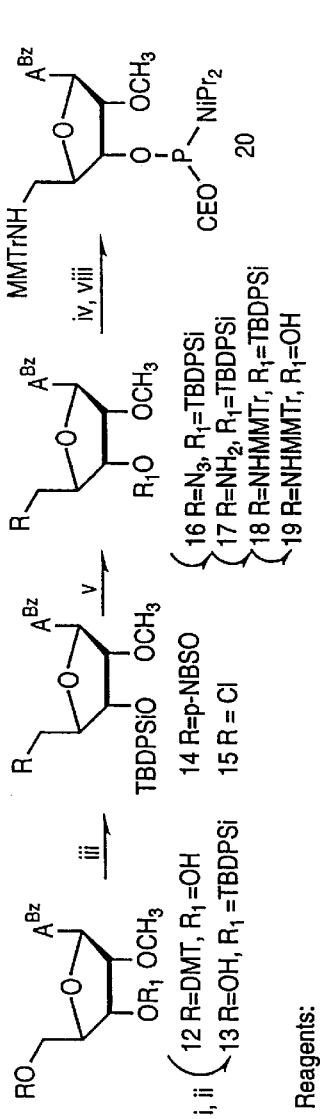
FIG. 8C.
Reagents:
i, TBDPSi-Cl/Im/DMF; ii, TFA/DCM; iii, p-nitrobenzenesulfonyl chloride/Pyr; iv, TBAF/THF; v, LiN₃/DMF/55°C; vi, MMTr-Cl/DMAP/Et₃N/Pyr; vii, 10% H₂/Pd-C/EtOH; viii, P(OCE)(NiPr₂)Cl/DIPEA/CH₂Cl₂.

*5'-deoxy-5'-mercapto-2'-O-methyluridine*
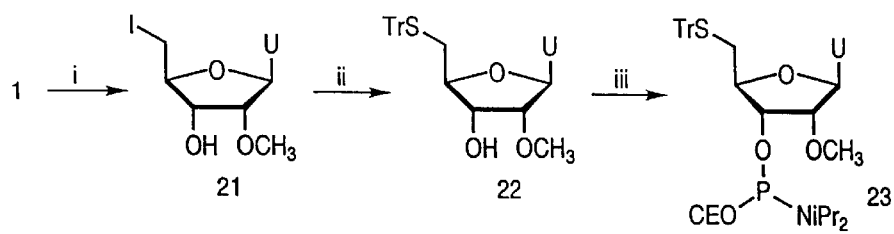
Reagents:
i, CH$_3$P(OC$_6$H$_5$)$_3$I/DMF; ii, TrSH/NaH/DMF; iii, P(OCE)(NiPr$_2$)Cl/DIPEA/CH$_2$Cl$_2$.
*5'-deoxy-5'-mercapto-2'-O-methylcytidine*
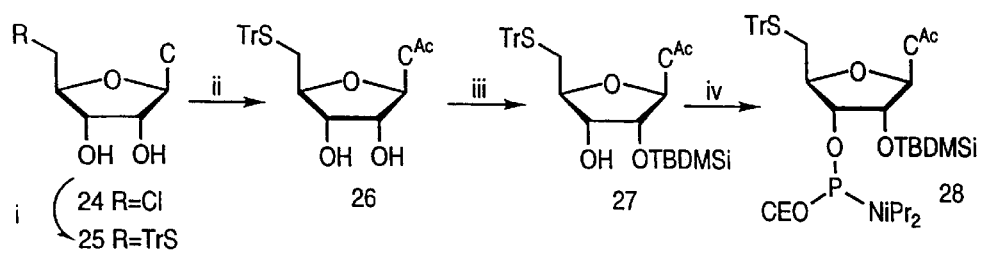
Reagents:
i, TrSH/NaOH/reflux; ii, Ac$_2$O/EtOH/reflux; iii, TBDMSi-Cl/Py/Im; iv, P(OCE) (NiPr$_2$)Cl/DIPEA/1-MeIm/CH$_2$Cl$_2$.
FIG. 8D.

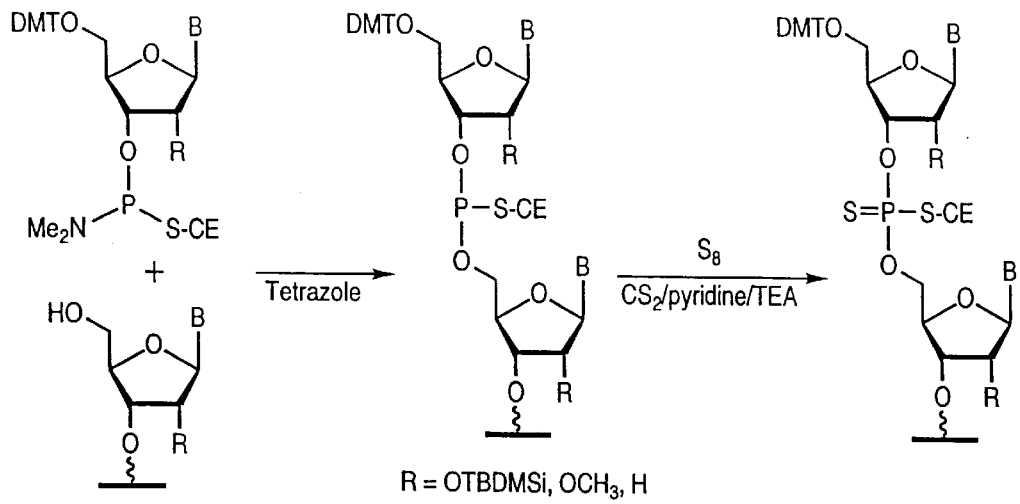
FIG. 12.
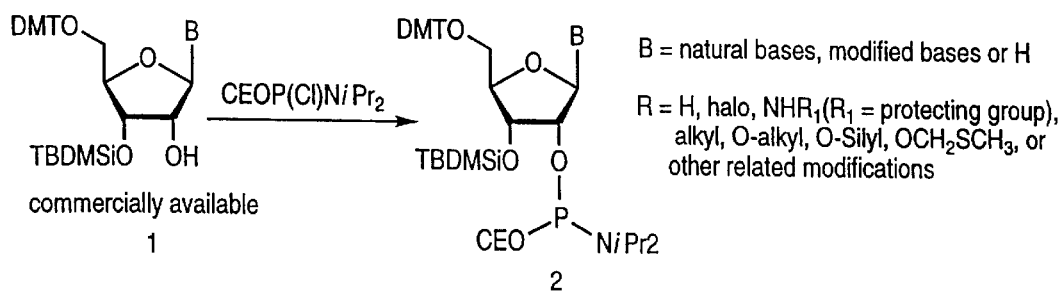
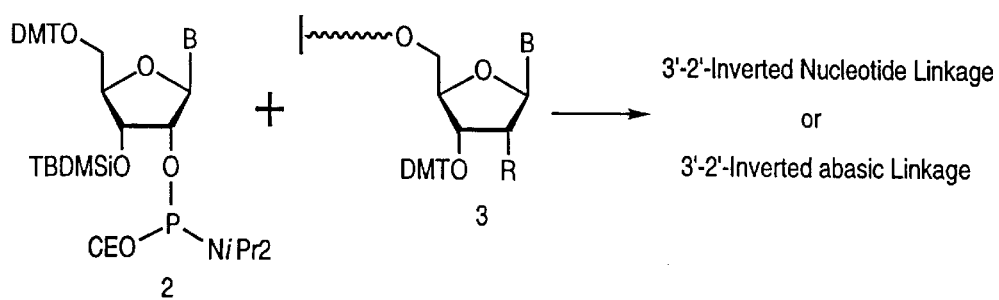
FIG. 13.

ENZYMATIC NUCLEIC ACIDS CONTAINING 5'-AND OR 3'-CAP STRUCTURES

RELATED APPLICATIONS

The Application is a continuation of U.S. Ser. No. 08/632,882, now U.S. Pat. No. 5,998,203, filed Apr. 16, 1996, the entirety of which, including the drawings, is hereby incorporated by reference herein.

BACKGROUND OF THE INVENTION

This invention relates to chemically synthesized ribozymes, or enzymatic nucleic acid molecules and derivatives thereof.

The following is a brief description of ribozymes. This summary is not meant to be complete but is provided only for understanding of the invention that follows. This summary is not an admission that all of the work described below is prior art to the claimed invention.

Ribozymes are nucleic acid molecules having an enzymatic activity which is able to repeatedly cleave other separate RNA molecules in a nucleotide base sequence-specific manner. Such enzymatic RNA molecules can be targeted to virtually any RNA transcript, and efficient cleavage achieved in vitro (Zaug et al., 324, Nature 429 1986 ; Kim et al., 84 *Proc. Natl. Acad. Sci. USA* 8788, 1987; Haseloff and Gerlach, 334 *Nature* 585, 1988; Cech, 260 *JAMA* 3030, 1988; and Jefferies et al., 17 *Nucleic Acids Research* 1371, 1989).

Because of their sequence-specificity, trans-cleaving ribozymes show promise as therapeutic agents for human disease (Usman & McSwiggen, 1995 *Ann. Rep. Med. Chem.* 30, 285–294; Christoffersen and Marr, 1995 *J. Med. Chem.* 38, 2023–2037). Ribozymes can be designed to cleave specific RNA targets within the background of cellular RNA. Such a cleavage event renders the mRNA non-functional and abrogate protein expression from that RNA. In this manner, synthesis of a protein associated with a disease state can be selectively inhibited.

Six basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over other technologies, since the effective concentration of ribozyme necessary to effect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base-pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base-pairing. Thus, it is thought that the specificity of action of a ribozyme is greater than that of antisense oligonucleotide binding the same RNA site.

Chemically-modified ribozymes can be synthesized which are stable in human serum for up to 260 hours (Beigelman et al., 1995 supra) and maintain near wild type (the chemically unmodified equivalent of a modified ribozyme) activity in vitro. A number of laboratories have reported that the enhanced cellular efficacy of phosphorothioate-substituted antisense molecules. The enhanced efficacy appears to result from either i) increased resistance to 5'-exonuclease digestion (De Clercq et al., 1970 *Virology* 42, 421–428; Shaw et al., 1991 *Nucleic Acids Res.* 19, 747–750), ii) intracellular localization to the nucleus (Marti et al., 1992 *Antisense Res. Dev.* 2, 27–39), or iii) sequence-dependent non-specific effects (Gao et al., 1992 *Molec. Pharmac.* 41, 223–229; Bock et al., 1992 *Nature* 355, 564–566; and Azad, et al., 1993 *Antimicrob. Agents Chemother.* 37, 1945–1954) which are not manifested in nonthioated molecules. Many effects of thioated compounds are probably due to their inherent tendency to associate non-specifically with cellular proteins such as the Sp1 transcription factor (Perez et al., 1994 *Proc. Natl Acad Sci. U.S.A.* 91, 5957–5961). Chemical modification of enzymatic nucleic acids that provide resistance to cellular 5'-exonuclease and 3'-exonuclease digestion without reducing the catalytic activity or cellular efficacy will be important for in vitro and in vivo applications of ribozymes.

Modification of oligonucleotides with a 5'-amino group offered resistance against 5'-exonuclease digestion in vitro (Letsinger & Mungall, 1970 *J. Org. Chem.* 35, 3800–3803).

Heidenreich et al., 1993 *FASEB J.* 7, 90 and Lyngstadaas et al., 1995 *EMBO. J.* 14, 5224, mention that hammerhead ribozymes with terminal phosphorothioate linkages can increase resistance against cellular exonucleases.

Seliger et al., Canadian Patent Application No. CA 2,106, 819 and *Prog. Biotechnol.* 1994, 9 (EC B6: Proceedings Of The 6th European Congress On Biotechnology, 1993, Pt. 2), 681–4 describe "oligoribonucleotide and ribozyme analogs with terminal 3'-3' and/or 5'-5' internucleotide linkages".

SUMMARY OF THE INVENTION

This invention relates to the incorporation of chemical modifications at the 5' and/or 3' ends of nucleic acids, which are particularly useful for enzymatic cleavage of RNA or single-stranded DNA. These terminal modifications are termed as either a 5'-cap or a 3'-cap depending on the terminus that is modified. Certain of these modifications protect the enzymatic nucleic acids from exonuclease degradation. Resistance to exonuclease degradation can increase the half-life of these nucleic acids inside a cell and improve the overall effectiveness of the enzymatic nucleic acids. These terminal modifications can also be used to facilitate efficient uptake of enzymatic nucleic acids by cells, transport and localization of enzymatic nucleic acids within a cell, and help achieve an overall improvement in the efficacy of ribozymes in vitro and in vivo.

The term "chemical modification" as used herein refers to any base, sugar and/or phosphate modification that will protect the enzymatic nucleic acids from degradation by nucleases. Non-limiting examples of some of the chemical modifications and methods for their synthesis and incorporation in nucleic acids are described in FIGS. 7, 8, 11–16 and infra.

In a preferred embodiment, chemical modifications of enzymatic nucleic acids are featured that provide resistance to cellular 5'-exonuclease and/or 3'-exonuclease digestion without reducing the catalytic activity or cellular efficacy of these nucleic acids.

In a second aspect, the invention features enzymatic nucleic acids with 5'-end modifications (5'-cap) having the formula:

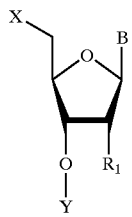

wherein, X represents H, alkyl, amino alkyl, hydroxy alkyl, halo, trihalomethyl [$CX_3$ (X=Br, Cl, F)], $N_3$, $NH_2$, NHR, $NR_2$ [each R is independently alkyl (C1–22), acyl (C1–22), or substituted (with alkyl, amino, alkoxy, halogen, or the like) or unsubstituted aryl], $NO_2$, $CONH_2$, COOR, SH, OR, ONHR, $PO_4^{2-}$, $PO_3S^{2-}$, $PO_2S_2^{2-}$, $POS_3^{2-}$, $PO_3NH^{2-}$, $PO_3NHR^-$, $NO_2$, $CONH_2$, COOR, B represents a natural base or a modified base or H; Y represents rest of the enzymatic nucleic acid; and R1 represents H, O-alkyl, C-alkyl, halo, NHR, or $OCH_2SCH_3$ (methylthiomethyl). The 5'-modified sugar synthesis is as described by Moffatt, in *Nucleoside Analogues:Chemistry, Biology and Medical Applications,* Walker, DeClercq, and Eckstein, Eds,; Plenum Press:New York, 1979, pp 71 (incorporated by reference herein).

Another preferred embodiment of the invention features enzymatic nucleic acid molecules having a 5'-cap, wherein said cap is selected from but not limited to, a group comprising, 4',5'-methylene nucleotide; 1-(β-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; L-nucleotide; α-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moeity; 5'-5'-inverted abasic moeity; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moeities (for more details see Beaucage and Iyer, 1993, Tetrahedron 49, 1925; incorporated by reference herein).

In a third aspect, the invention features enzymatic nucleic acids with 3'-end modifications (3'-cap) having the formula:

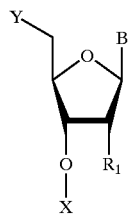

wherein, X represents 4'-thio nucleotide, carbocyclic nucleotide; 1,5-anhydrohexitol nucleotide; L-nucleotides; α-nucleotides; modified base nucleotide; phosphorodithioate linkage; threopentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moeity; 3'-3'-inverted abasic moeity; 3'-2'-inverted nucleotide moeity; 3'-2'-inverted abasic moeity; 1,4-butanediol; 3'-phosphoramidate; hexylphosphate; aminohexyl phosphate; 3'-phosphate; 3'-phosphorothioate; or bridging or nonbridging methylphosphonate moeity; B represents a natural base or a modified base or H; Y represents rest of the enzymatic nucleic acid; and R1 represents H, O-alkyl, C-alkyl, halo, NHR [R=alkyl (C1–22), acyl (C1–22), substituted or unsubstituted aryl], or $OCH_2SCH_3$ (methylthiomethyl).

In yet another preferred embodiment the invention features enzymatic nucleic acid molecules having a 3'-cap, wherein said cap is selected from but not limited to, a group comprising, 4'-thio nucleotide, carbocyclic nucleotide; 1,5-anhydrohexitol nucleotide; L-nucleotides; a-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moeity; 3'-3'-inverted abasic moeity; 3'-2'-inverted nucleotide moeity; 3'-2'-inverted abasic moeity; 1,4-butanediol phosphate; 3'-phosphoramidate; hexylphosphate; aminohexyl phosphate; 3'-phosphate; 3'-phosphorothioate; phosphorodithioate; or bridging or nonbridging methylphosphonate moeity (for more details see Beaucage and Iyer, 1993, Tetrahedron 49, 1925; incorporated by reference herein).

In a fourth aspect, the invention features enzymatic nucleic acids with both 5'-cap and a 3'-cap which may be same or different.

The term "nucleotide" is used as recognized in the art to include natural bases, and modified bases well known in the art. Such bases are generally located at the 1' position of a sugar moiety. Nucleotide generally comprise a base, sugar and a phosphate group. The nucleotide can be unmodified or modified at the sugar, phosphate and/or base moeity. The term "abasic" or "abasic nucleotide" as used herein encompasses sugar moieties lacking a base or having other chemical groups in place of base at the 1' position.

By the phrase "enzymatic nucleic acid" is meant a catalytic modified-nucleotide-containing nucleic acid molecule that has complementarity in a substrate binding region to a specified gene target, and also has an enzymatic activity that specifically cleaves RNA or DNA in that target. That is, the enzymatic nucleic acid is able to intramolecularly or intermolecularly cleave RNA or DNA and thereby inactivate a target RNA or DNA molecule. This complementarity functions to allow sufficient hybridization of the enzymatic RNA molecule to the target RNA or DNA to allow the cleavage to occur. 100% Complementarity is preferred, but complementarity as low as 50–75% may also be useful in this invention. The nucleic acids may be modified at the base, sugar, and/or phosphate groups. The term enzymatic nucleic acid is used interchangeably with phrases such as ribozymes, catalytic RNA, enzymatic RNA, catalytic DNA, nucleozyme, DNAzyme, RNA enzyme, endoribonuclease, minizyme, leadzyme or DNA enzyme. All of these terminologies describe nucleic acid molecules with enzymatic activity.

There are several examples of modified bases as it relates to nucleic acids, is well known in the art and has recently been summarized by Limbach et al., 1994, *Nucleic Acids Res.* 22, 2183. Some of the non-limiting examples of base modifications that can be introduced into enzymatic nucleic acids without significantly effecting their catalytic activity include, pyridin-4-one, pyridin-2-one, phenyl, pseudouracil, 2,4,6-trimethoxy benzene, 3-methyluracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine); Guanosine or adenosine residues may be replaced by diaminopurine residues in either the core or stems.

There are several examples in the art describing sugar modifications that can be introduced into enzymatic nucleic acid molecules without significantly effecting catalysis and significantly enhancing their nuclease stability and efficacy. Sugar modification of enzymatic nucleic acid molecules have been extensively described in the art (see Eckstein et al., International Publication PCT No. WO 92/07065; Perrault et al. *Nature* 1990, 344,565–568; Pieken et al. *Science* 1991, 253, 314–317; Usman and Cedergren, *Trends in Biochem. Sci.* 1992, 17, 334–339; Usman et al. International Publication PCT No. WO 93/15187; Sproat, U.S. Pat. No. 5,334,711 and Beigelman et al., 1995 *J. Biol. Chem.* 270, 25702). Such publications describe the location of incorporation of modifications and the like, and are incorporated by reference herein. In view of such teachings, similar modifications can be used as described herein.

Specifically, an "alkyl" group refers to a saturated aliphatic hydrocarbon, including straight-chain, branched-chain, and cyclic alkyl groups. Preferably, the alkyl group has 1 to 12 carbons. More preferably it is a lower alkyl of from 1 to 7 carbons, more preferably 1 to 4 carbons. The alkyl group may be substituted or unsubstituted. When substituted the substituted group(s) is preferably, hydroxyl, cyano, alkoxy, =O, =S, NO$_2$ or N(CH$_3$)$_2$, amino, or SH. The term also includes alkenyl groups which are unsaturated hydrocarbon groups containing at least one carbon-carbon double bond, including straight-chain, branched-chain, and cyclic groups. Preferably, the alkenyl group has 1 to 12 carbons. More preferably it is a lower alkenyl of from 1 to 7 carbons, more preferably 1 to 4 carbons. The alkenyl group may be substituted or unsubstituted. When substituted the substituted group(s) is preferably, hydroxyl, cyano, alkoxy, =O, =S, NO$_2$, halogen, N(CH$_3$)$_2$, amino, or SH. The term "alkyl" also includes alkynyl groups which have an unsaturated hydrocarbon group containing at least one carbon-carbon triple bond, including straight-chain, branched-chain, and cyclic groups. Preferably, the alkynyl group has 1 to 12 carbons. More preferably it is a lower alkynyl of from 1 to 7 carbons, more preferably 1 to 4 carbons. The alkynyl group may be substituted or unsubstituted. When substituted the substituted group(s) is preferably, hydroxyl, cyano, alkoxy, =O, =S, NO$_2$ or N(CH$_3$)$_2$, amino or SH.

Such alkyl groups may also include aryl, alkylaryl, carbocyclic aryl, heterocyclic aryl, amide and ester groups. An "aryl" group refers to an aromatic group which has at least one ring having a conjugated π electron system and includes carbocyclic aryl, heterocyclic aryl and biaryl groups, all of which may be optionally substituted. The preferred substituent(s) of aryl groups are halogen, trihalomethyl, hydroxyl, SH, OH, cyano, alkoxy, alkyl, alkenyl, alkynyl, and amino groups. An "alkylaryl" group refers to an alkyl group (as described above) covalently joined to an aryl group (as described above. Carbocyclic aryl groups are groups wherein the ring atoms on the aromatic ring are all carbon atoms. The carbon atoms are optionally substituted. Heterocyclic aryl groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted. An "amide" refers to an —C(O)—NH—R, where R is either alkyl, aryl, alkylaryl or hydrogen. An "ester" refers to an —C(O)—OR', where R is either alkyl, aryl, alkylaryl or hydrogen.

The 5'-cap and/or 3'-cap derivatives of this invention provide enhanced activity and stability to the enzymatic nucleic acids containing them.

By "complementarity" is meant a nucleic acid that can form hydrogen bond(s) with other RNA sequence by either traditional Watson-Crick or other non-traditional types (for example, Hoogsteen type) of base-paired interactions.

By "bridging" and "nonbridging" are meant to indicate the relative positions of oxygen atom involved in the formation of standard phosphodiester linkage in a nucleic acid. These backbone oxygen atoms can be readily modified to impart resistance against nuclease digestion. The terms are further defined as follows:

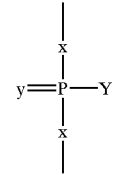

wherein "x" is bridging oxygen and 'y' is nonbridging oxygen.

In preferred embodiments of this invention, the enzymatic nucleic acid molecule is formed in a hammerhead or hairpin motif, but may also be formed in the motif of a hepatitis delta virus (HDV), group I intron, RNaseP RNA (in association with an RNA guide sequence) or *Neurospora* VS RNA. Examples of such hammerhead motifs are described by Rossi et a., 1992, *Aids Research and Human Retroviruses* 8, 183, of hairpin motifs by Hampel et a/., EP0360257, Hampel and Tritz, 1989 *Biochemistry* 28,4929, and Hampel et al., 1990 *Nucleic Acids Res.* 18, 299, and an example of the hepatitis delta virus motif is described by Perrotta and Been, 1992 *Biochemistry* 31, 16; of the RNaseP motif by Guerrier-Takada et al., 1983 *Cell* 35, 849 and Forster and Altman, 1990 *Science* 249, 783, *Neurospora* VS RNA ribozyme motif is described by Collins (Saville and Collins, 1990 *Cell* 61, 685–696; Saville and Collins, 1991 *Proc. Natl. Acad. Sci. USA* 88, 8826–8830; Guo and Collins, 1995 *EMBO J.* 14, 368) and of the Group I intron by Cech et a/., U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

The invention provides a method for producing a class of enzymatic cleaving agents which exhibit a high degree of specificity for the RNA of a desired target. The enzymatic nucleic acid molecule is preferably targeted to a highly conserved sequence region of a target such that specific treatment of a disease or condition can be provided with a single enzymatic nucleic acid. Such enzymatic nucleic acid molecules can be delivered exogenously to specific cells as required. In the preferred hammerhead motif the small size (less than 60 nucleotides, preferably between 30–40 nucleotides in length) of the molecule allows the cost of treatment to be reduced compared to other ribozyme motifs.

Synthesis of nucleic acids greater than 100 nucleotides in length is difficult using automated methods, and the therapeutic cost of such molecules is prohibitive. In this invention, small enzymatic nucleic acid motifs (e.g., of the hammerhead structure) are used for exogenous delivery. The simple structure of these molecules increases the ability of the enzymatic nucleic acid to invade targeted regions of the mRNA structure. Unlike the situation when the hammerhead structure is included within longer transcripts, there are no non-enzymatic nucleic acid flanking sequences to interfere with correct folding of the enzymatic nucleic acid structure or with complementary regions.

Therapeutic ribozymes must remain stable within cells until translation of the target mRNA has been inhibited long enough to reduce the levels of the undesirable protein. This period of time varies between hours to days depending upon the disease state. Clearly, ribozymes must be resistant to nucleases in order to function as effective intracellular therapeutic agents. Improvements in the chemical synthesis of RNA (Wincott et al., 1995 *Nucleic Acids Res.* 23, 2677; incorporated by reference herein) have expanded the ability to modify ribozymes to enhance their nuclease stability. The majority of this work has been performed using hammerhead ribozymes (reviewed in Usman and McSwiggen, 1995 supra) and can be readily extended to other ribozyme motifs.

Other features and advantages of the invention will be apparent from the following description of the preferred embodiments thereof, and from the claims.

DESCRIPTION OF THE PREFERRED EMBODIMENTS

The drawings will first briefly be described.
Drawings:

FIG. 1 is a diagrammatic representation of the hammerhead ribozyme domain (SEQ ID Nos. 1 and 2) known in the art. Stem II can be $\geq 2$ base-pair long. Each N is independently any base or non-nucleotide as used herein.

FIG. 2a is a diagrammatic representation of the hammerhead ribozyme domain known in the art; FIG. 2b is a diagrammatic representation of the hammerhead ribozyme as divided by Uhlenbeck (1987, *Nature,* 327,596–600) into a substrate and enzyme portion; FIG. 2c is a similar diagram showing the hammerhead divided by Haseloff and Gerlach (1988, *Nature,* 334,585–591) into two portions; and FIG. 2d is a similar diagram showing the hammerhead divided by Jeffries and Symons (1989, *Nucl. Acids. Res.,* 17, 1371–1371) into two portions.

FIG. 3 is a diagrammatic representation of the general structure of a hairpin ribozyme (SEQ ID No. 4) and substrate RNA (SEQ ID No. 3). Helix 2 (H2) is provided with a least 4 base pairs (i.e., n is 1, 2, 3 or 4) and helix 5 can be optionally provided of length 2 or more bases (preferably 3–20 bases, i.e., m is from 1–20 or more). Helix 2 and helix 5 may be covalently linked by one or more bases (i.e., r is $\geq 1$ base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is $\geq 2$ bases. The connecting loop can also be replaced with a non-nucleotide linker molecule. H refers to bases A, U, or C. Y refers to pyrimidine bases. "_____" refers to a covalent bond.

FIG. 4 is a representation of the general structure of the hepatitis delta virus ribozyme domain (SEQ ID No. 5) known in the art. In each instance, each N and N' independently is any normal or modified base and each dash represents a potential base-pairing interaction. These nucleotides may be modified at the sugar, base or phosphate.

FIG. 5 is a representation of the general structure of the self-cleaving VS RNA ribozyme domain (SEQ ID No. 6).

FIG. 6 is a diagrammatic representation of a hammerhead ribozyme-substrate complex (SEQ ID Nos. 8 and 7). The ribozyme is targeted against site 575 within c-myb RNA. Lowercase alphabets indicate 2'-O-methyl substitution; uppercase alphabets indicate ribonucleotides; Arrow indicates the site of RNA cleavage; u4 and u7, represent modification with 2'-amino group; X and Z represent 5'- and 3'-caps which may be the same or different.

FIG. 7A) is a general formula for 5'-end modifications. B) chemical structures of a few of the 5'-end modifications. C) diagrammatic representation of a 5'-5'-inverted abasic moiety.

FIG. 8A) diagrammatic representation of 5'-phosphoramidate and 5'-phosphorothioate linkages; B) a synthesis scheme for 5'-amino-5'-deoxy-2'-O-methyl uridine and guanosine phosphoramidites; C) a synthesis scheme for 5'-amino-5'-deoxy-2'-O-methyl adenosine phosphoramidites; D) a synthesis scheme for 5'-deoxy-5'-mercapto-2'-O-methyl uridine and cytidine phosphoramidites.

FIG. 9 shows ribozyme-mediated inhibition of smooth muscle cell proliferation. The hammerhead (HH) ribozymes, targeted to site 575 within c-myb RNA, as shown in FIG. 6, were chemically modified such that the ribozyme consists of ribose residues at five positions; U4 and U7 positions contain 2'-NH$_2$ modifications, the remaining nucleotide positions contain 2'-O-methyl substitutions. Additionally, the 5'-end of the ribozyme contains 5'-amino modification and the 3' end of the ribozyme contains a 3'-3' linked inverted abasic deoxyribose (designated as 3'-iH). Inactive ribozyme (5'-amino Inactive RZ) with G5 to U and A14 to U substitution was synthesized and used as a negative control.

FIG. 10 shows ribozyme-mediated inhibition of smooth muscle cell proliferation. The hammerhead (HH) ribozymes, targeted to site 575 within c-myb RNA, as shown in FIG. 6, were chemically modified such that the ribozyme consists of ribose residues at five positions; U4 position contains 2'-C-allyl modification, the remaining nucleotide positions contain 2'-O-methyl substitutions. Additionally, the 5'-end of the ribozyme contains amino modification and the 3' end of the ribozyme contains a 3'-3' linked inverted abasic deoxyribose (designated as 3'-iH). Inactive ribozyme (5'-amino Inactive RZ) with G5 to U and A14 to U substitution was synthesized and used as a negative control.

FIG. 11A) chemical structures of a few of the 3'-end modifications. B) diagrammatic representation of a few 3'-end mofication linkages.

FIG. 12 is a synthesis scheme for phosphorodithioate linkages.

FIG. 13 is a synthesis scheme for 3'-2'-inverted nucleoside or an abasic nucleoside linkages. Compound 2 can be reacted with compound 3 to yield either a 3'-2'-inverted nucleotide linkage as shown in FIG. 11B, infra, or a 3'-2'-inverted abasic ribose, deoxyribose or variations thereof (see FIG. 11B).

Figure 18:
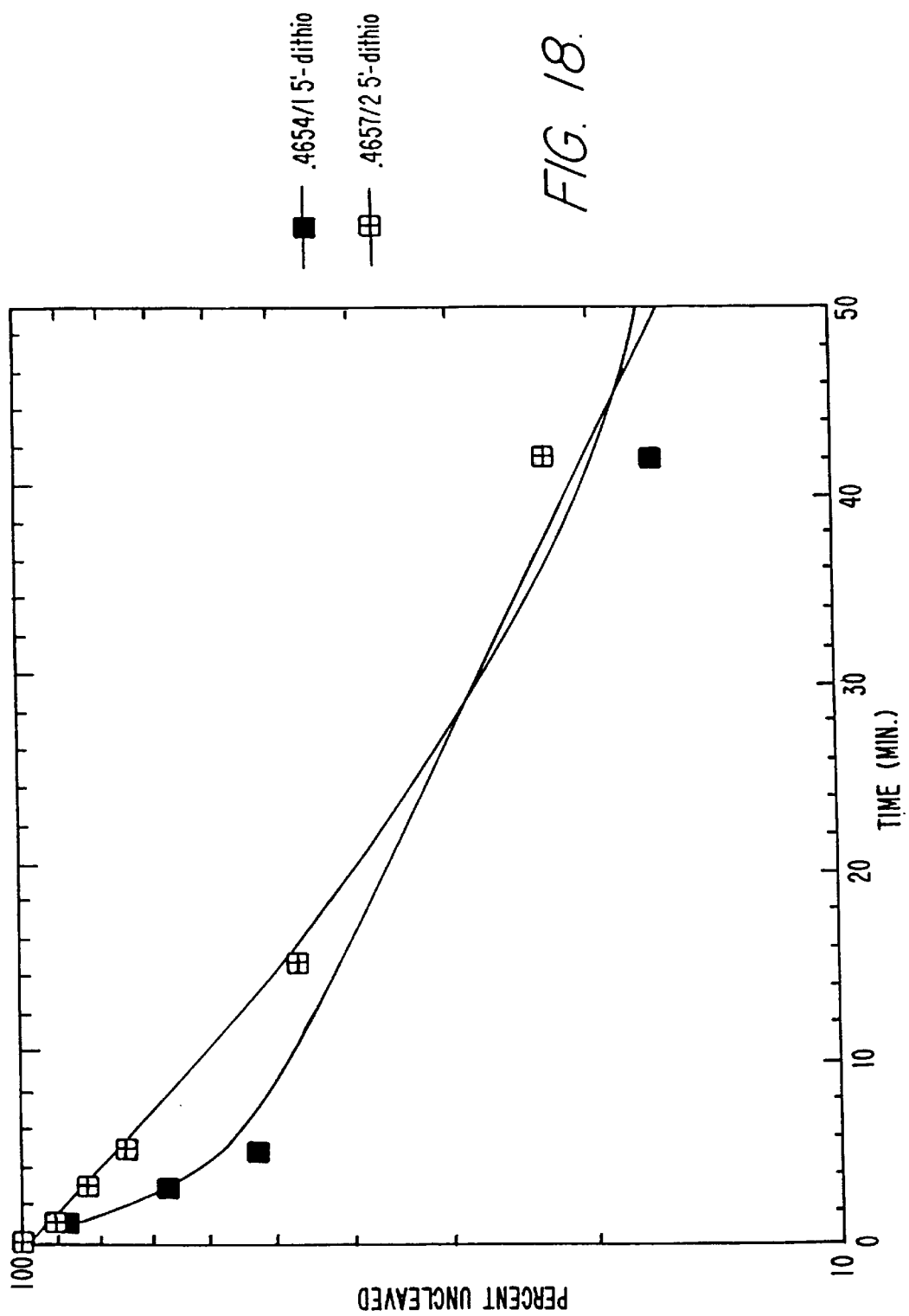

FIG. 18 is a graphical representation of RNA cleavage reaction catalyzed by hammerhead ribozymes containing either one or two 5'-terminal phosphorodithioate modifications. Ribozyme 0.4654/1 5'-dithio, represents a hammerhead ribozyme targeted to c-myb site 575 as shown in FIG. 6, and were chemically modified such that the ribozyme consists of ribose residues at five positions; U4 position contains 2'-C-allyl modification, the remaining nucleotide positions contain 2'-O-methyl substitutions. Additionally, the 5'-end of the ribozyme contains one phosphorodithioate modification and the 3' end of the ribozyme contains a 3'-3' linked inverted abasic deoxyribose (designated as 3'-iH). Ribozyme 0.4657/2 5'-dithio, represents a hammerhead ribozyme targeted to c-myb site 575 as shown in FIG. 6, and were chemically modified such that the ribozyme consists of ribose residues at five positions; U4 position contains 2'-C-allyl modification, the remaining nucleotide positions contain 2'-O-methyl substitutions. Additionally, the 5'-end of the ribozyme contains two phosphorodithioate modification and the 3' end of the ribozyme contains a 3'-3' linked inverted abasic deoxyribose (designated as 3'-iH).

NUCLEOTIDES AND NUCLEOSIDES

Figure 1:
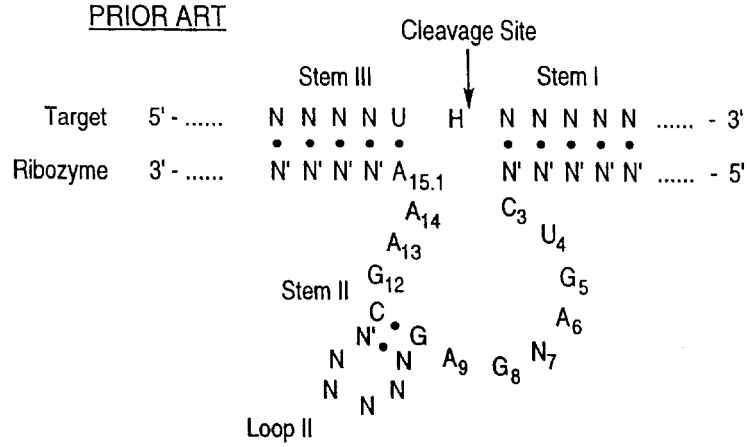

Applicant has found that chemical modifications of this invention are particulary useful for enzymatic nucleic acid molecule stabilization. Thus, below is provided examples of one such molecule, a hammerhead ribozyme. Those in the art will recognize that equivalent procedures can be used to make other enzymatic nucleic acid molecules having a 5'- and/or 3'-cap structure. Specifically, FIGS. 1 and 6 show base numbering of a hammerhead motif in which the numbering of various nucleotides in a hammerhead ribozyme is provided. This is not to be taken as an indication that the FIGure is prior art to the pending claims, or that the art discussed is prior art to those claims.

EXAMPLES

The following are non-limiting examples showing the synthesis and activity of enzymatic nucleic acids containing 5'- and/or 3'-cap modifications and the synthesis of monomer phosphoramidites.

Example 1

Synthesis of Enzymatic Nucleic Acids Containing 5'- and/or 3'-cap Structures

The method of synthesis follows the procedure for normal RNA synthesis as described in Usman,N.; Ogilvie,K. K.; Jiang,M.-Y.; Cedergren,R. J. *J. Am. Chem. Soc.* 1987, 109, 7845–7854; Scaringe,S. A.; Franklyn,C.; Usman,N. *Nucleic Acids Res.* 1990, 18,5433–5441; and Wincott et al., 1995, *Nucleic Acids Res.* 23, 2677 (all of these references are incorporated by reference herein in their entirety) and makes use of common nucleic acid protecting and coupling groups, such as dimethoxytrityl at the 5'-end, -and phosphoramidites at the 3'-end. Phosphoramidites of the 5'-cap and/or 3'-cap structures selected from those described and illustrated in FIGS. 7–8 and 11–16 may be incorporated not only into hammerhead ribozymes, but also into hairpin, hepatitis delta virus, VS RNA, RNase P ribozyme, Group I or Group II intron catalytic nucleic acids. They are, therefore, of general use in any enzymatic nucleic acid structure.

Example 2

Incorporation of 5'-Amino- and 5'-Mercapto-5'-Deoxy-2'-O-Methyl Nucleosides Into Hammerhead Ribozymes Non-chiral phosphoramidate and phosphorothioate linkages (FIG. 8) for incorporation at the 5'-end of a hammerhead ribozyme are described infra. These linkages are electronically and sterically similar to their natural congener and introduction of a single 3'-O—P(O)(O⁻)—NH-5' or 3'-O—P(O)(O⁻)—S5' link at the 5'-end of the ribozyme has little effect on its hybridization to a substrate and/or ribozyme cleavage activity. Letsinger and Mungall, *J. Org. Chem.* 1970, 35, 3800–3803, reported the synthesis of a thymidine dimer and trimer possessing internucleotide phosphoramidate bonds 3'-O—P(O)(O⁻)—NH-5' which were stable in neutral and alkaline conditions and showed increased stability against exonucleases. The terminal 5'-amino group of a thymidine dimer was found to efficiently inhibit the action of spleen phosphodiesterase. It is also reported that introduction of a phosphoramidate 3'-NH—P(O)(O⁻)—O-5' leads to enhancement in stability of the heteroduplex (Gryaznov and Letsinger, *Nucleic Acids Res.* 1992, 20, 3403–3409). While studies of 3'-S-modified oligodeoxynucleotides demonstrated complete resistance to cleavage by EcoRV, there are no related studies on 5'-S-modified oligonucleotides (Vyle et al., *Biochemistry* 1992, 31, 3012–3018). Although there is interest in the synthesis, chemical and biological properties of oligonucleotides with bridging 5'-N (Letsinger et al., supra; Mag and Engels, *Tetrahedron* 1994, 50, 10225–10234; Gryaznov and Sokolova, *Tetrahedron Lett.* 1990, 31, 3205–3208; Letsinger et al., *Nucleic Acids Res.* 1976, 3, 1053–1063; Mag, and Engels, *Nucleosides & Nucleotides* 1988, 7, 725–728) and 5'-S (Sund and Chattopadhyaya, *Tetrahedron* 1989, 45, 7523–7544; Chladek amnd Nagyvary, *Amer. Chem. Soc.* 1972, 94, 2079–2085; Cook, *J. Amer. Chem. Soc.* 1970, 92, 190–195; Liu and Reese, *Tetrahedron Lett.* 1995, 36, 3413–3416) substitutions as well as 3'-N (Mag et al., *Tetrahedron Lett.* 1992, 33, 7319–7322; Zielinski and Orgel, *Nucleic Acids Res.* 1987, 15, 1699–1715) and 3'-S (Cosstick and Vyle, *Nucleic Acids Res.* 1990, 18, 829–835; Li et al., *Tetrahedron* 1992, 48, 2729–2738; and *J. Chem. Soc.* Perkin I 1994, 2123–2129; Liu and Reese, *Tetrahedron Lett.* 1996, 37, 925–928) modified oligonucleotides, there are few reports (Bannwarth, *Helv. Chim. Acta* 1988, 71, 1517–1427;

Mag and Engels, *Nucleic Acids Res.* 1989, 17,5973–5988; Mag et al., *Nucleic Acids Res.* 1991, 19, 1437–1441; Chen et al., *Nucleic Acids Res.* 1995, 23, 2661–2668; Cosstick and Vyle *Tetrahedron Lett.* 1989, 30, 4693–4696) of the step-by-step elongation on solid support using 5'- or 3'-N(S)-modified nucleotide monomers.

Because of the different chemical nature of N—R and S—R bonds compared to O—R bonds there is a requirement for introduction of special protecting groups for amino and thiol functions and special conditions for their cleavage, considerably different from those routinely used in a solid phase nucleic acid synthesis, but still compatible with solid phase phosphoramidite chemistry. Also, optimization of the synthetic cycle for the introduction of the modified monomers is usually necessary.

Based on previous investigations in the 2'-deoxy series (Mag et al., 1989 and 1991 supra) we have chosen 4-methoxytrityl (MMTr) group for the protection of the 5'-amino function while the trityl (Tr) group was used for the protection of the 5'-mercapto functionality in modified monomers.

The synthesis of 5'-amino-5'-deoxy-2'-O-methyl-uridine, guanosine and adenosine 3'-phosphoramidites 5, 11 and 20 (FIGS. 8B and 8C), as well as 5'-mercapto-5'-deoxy-2'-O-methyl-uridine and cytidine 3'-phosphoramidite 23 and 28 (FIG. 8D) and their incorporation into ribozymes are described infra. Extensive modification of hammerhead ribozyme with 2'-O-Me-nucleosides resulted in a catalytic motif with almost wild type cleavage activity and considerably improved nuclease stability has recently been described (Beigelman et al., *J. Biol. Chem.* 1995, 270, 25702–25708). Another reason for using 2'-O-methyl modified nucleotides is to prevent degradation of oligonucleotides by attack of the free neighboring 2'-hydroxyl on the phosphorus during deprotection, a well documented event in the case of 5'-S-modified ribonucleoside dimers.

Materials and Methods

General Methods

2'-O-Methyluridine, $N^2$-isobutyryl-2'-O-methylguanosine and 5'-O-(4,4'-dimethoxytrityl)-$N^6$-benzoyl-2'-O-methyladenosine were obtained from ChemGenes Corporation (Waltham, Mass.). All NMR spectra were recorded on a Varian Gemini 400 spectrometer operating at 400.075 MHz for proton and 161.947 MHz for phosphorus. Chemical shifts in ppm refer to TMS and $H_3PO_4$, respectively. The solvent was $CDCl_3$ if not stated otherwise. The standard work up consisted of partitioning of the residue after removal of solvents between 5% aqueous $NaHCO_3$ and $CH_2Cl_2$ followed by washing of the organic layer with brine, drying over $Na_2SO_4$ and removal of solvents in vacuo. Analytical thin-layer chromatography (TLC) was performed with Merck Art. 5554 Kieselgel 60 $F_{254}$ plates and column chromatography using Merck 0.040–0.063 mm Silica gel 60. Melting temperatures were determined on the Electrothermal Model IA 9200 apparatus and are uncorrected.

The general procedures for RNA synthesis and deprotection have been described previously (Wincott et al., supra, incorporated by reference herein in its entirety) Syntheses were conducted on a 394 (ABI) synthesizer using a modified 2.5 μmol scale protocol with a 5 min coupling step for 2'-O-TBDMSi protected nucleotides and 2.5 min coupling step for 2'-O-methyl nucleotides. A 6.5-fold excess of a 0.1 M solution phosphoramidite and a 24-fold excess of S-ethyl tetrazole relative to polymer-bound 5'-hydroxyl was used in each coupling cycle.

All analytical HPLC analyses were performed on a Hewlett Packard 1090 HPLC with a Dionex NucleoPac® PA-100 column, 4×250 mm, at 50° C., as reported (Wincott et al., supra).

CGE analyses were performed on a Hewlett Packard $^{3D}$CE with a J & W μPAGE ™-5 (5% T, 5% C) polyacrylamide gel-filled column, 75 μm I.D.×75 cm, 50 cm effective length, 100 mM Tris-Borate, 7 M Urea, pH=8.3, and J & W μPAGE ™ Buffer (100 mM Tris-Borate, 7 M Urea, pH=8.3). Samples were electrokinetically injected using −13 kV for 3–10 sec, run at −13 kV and detected at 260 nm.

MALDI-TOF mass spectra were determined on a PerSeptive Biosystems Voyager spectrometer.

Synthesis of Monomer Building Blocks

Figure 5:
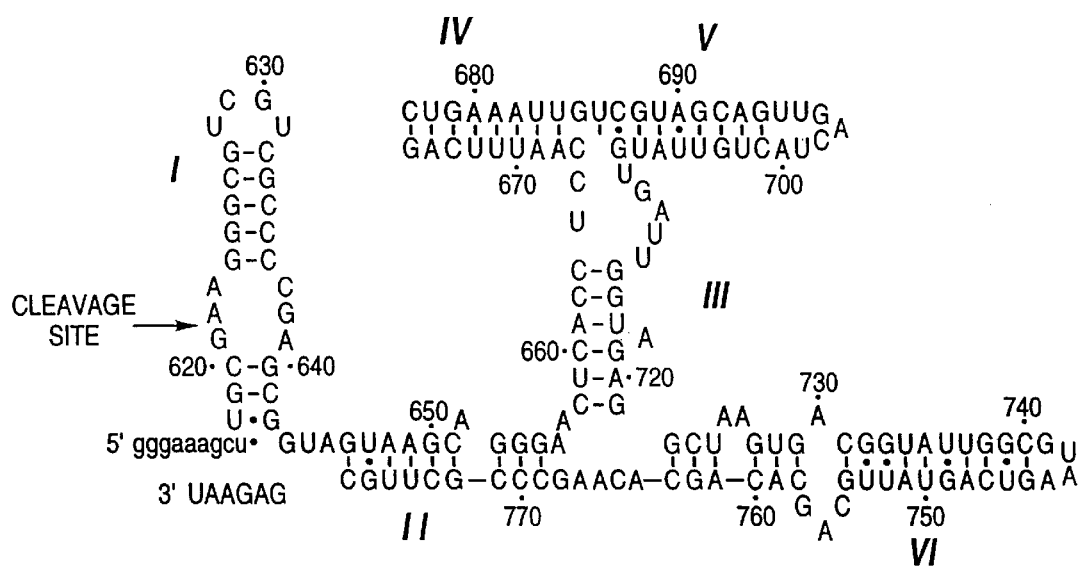
Figure 8A:
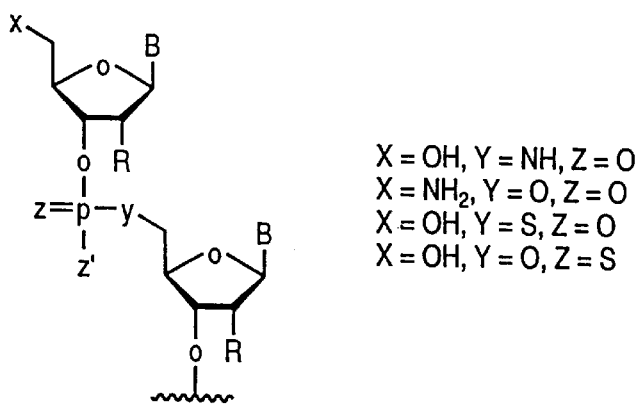

Referring to FIG. 8B, 5'-Azido-5'-deoxy-2'-O-methyluridine (2) was synthesized from 2'-O-methyluridine (1) in 79% yield (white foam) according to the procedure of Yamamoto et al., *J. Chem. Soc.* Perkin I 1978, 306–310 (incorporated by reference herin in its entirety), for the preparation of 5'-azido-5'-deoxythymidine, $^1$H NMR δ9.16 (br s, 1H, NH), 7.70 (d, $J_{6,5}$=8.2, 1H, H6), 5.97 (d, $J_{1',2}$=2.2, 1H, H1'), 5.87 (d, $J_{5,6}$=8.2, 1H), H5), 4.21 (m, 1H,H3'), 4.08 (m, 1H, H2'), 3.92 (dd, $J_{5',4'}$=2.2, $J_{5',5''}$=13.4, 1H, H5'), 3.87 (dd, $J_{4',5'}$=2.2, $J_{4',3'}$=5.6, 1H, H4'), 3.82 (dd, $J_{5'',4'}$=3.3, $J_{5'',5'}$=13.4, 1H, H5''), 3.67 (s, 3H, OMe).

5'-Amino-5'-deoxy-2'-O-methyluridine (3) (FIG. 8B) was synthesized from 2 according to a modification of the procedure of Mag and Engels, *Nucleic Acids Res.* 1989, 17, 5973–5988 (incorporated by reference herin in its entirety), for the preparation of 5'-amino-5'-deoxythymidine: 2 (680 mg, 2.27 mmol) was dissolved in dry pyridine (5 mL) and triphenylphosphine ($Ph_3P$) (890 mg, 3.39 mmol) was added. The mixture was stirred for 2 h at rt at which time all the starting material had reacted. Concentrated $NH_4OH$ (2 mL) was then added and the mixture stirred at rt for 2 h. Solvents were removed at reduced pressure, water was added (20 mL) and precipitate removed by filtration. The filtrate was extracted with benzene and ether and then evaporated to dryness. The residue was dissolved in isopropanol from which the amorphous solid precipitated on cooling (480 mg, 82%), $^1$H NMR (dmso-$d_6$) δ8.01 (d, $J_{6,5}$=8.1, 1H, H6), 5.90 (d, $J_{1',2'}$=5.2, 1H, H1'), 5.71 (d, $J_{5,6}$=8.1, 1H, H5), 4.16 (app t, $J_{3',4'}$=5.0, 1H, H3'), 3.91 (app t, $J_{2',1'}$=5.2, 1H, H2'), 3.84 (q, $J_{4',3'}$=5.0, 1H, H4'), 3.43 (s, 3H, OMe), 2.88 (dd, $J_{5',4'}$=4.5, $J_{5',5''}$=13.7, 1H, H5'), 2.83 (dd, $J_{5'',4'}$=5.0, $J_{5'',5'}$=13.7, 1H, H5'').

5'-N-(4-Methoxytrityl)amino-5'-deoxy-2'-O-methyluridine (4) (FIG. 8B) was synthesized from 3 using 4-methoxytrityl chloride/DMAP/$Et_3$N/Pyr in 63% yield according to the procedure of Mag and Engels, *Nucleic Acids Res.* 1989, 17, 5973–5988, and is incorporated by reference herin in its entirety. $^1$H NMR δ8.25 (br s, 1H, NH), 7.54–6.88 (m, 15H, aromatic, H6), 5.96 (s, 1H, H1'), 5.70 (d, $J_{5,6}$=7.9, 1H, H5), 4.13 (m, 1H, H3'), 4.01 (m, 1H, H2'), 3.86 (s, 3H, TrOMe), 3.77 (m, 1H, H4'), 3.69 (s, 3H, OMe), 2.82 (dd, $J_{5',4'}$=2.9, $J_{5'',5'}$=12.9, 1H, H5'), 2.66 (d, $J_{NH,5'}$=8.8, 1H, 5'NH), 2.42 (dd, $J_{5'',4'}$=6.8, $J_{5'',5'}$=12.9, 1H, H5'').

5'-N-(4-Methoxytrityl)amino-5'-deoxy-2'-O-methyluridine-3'-O-(2-cyanoethyl-N,N-diisopropylphosphoramidite) (5). (see FIG. 8B) To the solution of 4 (520 mg, 0.98 mmol) and N,N-diisopropylethylamine (DIPEA) (0.34 mL, 1.95 mmol) in $CH_2Cl_2$ (10 mL) under argon was added 2-cyanoethyl N,N-diisopropylchlorophosphoramidite (0.30 mL, 1.34 mmol) was added dropwise, stirring was continued for 3 h at rt. The reaction mixture was then cooled to 0° C., dry MeOH (3 mL) was added and stirring continued for 5 min. The mixture was evaporated to dryness in vacuo (40° C. bath temp) and the residue chromatographed on a silica gel column using 20–70% gradient EtOAc in hexane (1% $Et_3$N) to afford 5 as a colorless foam (0.60 g, 83%), $^{31}$P NMR δ148.97 (s) and 148.67 (s).

5'-O-p-Toluenesulfonyl-N²-isobutyryl-2'-O-methylguanosine (7). (see FIG. 8B) N²-Isobutyryl-2'-O-methylguanosine (6) (Inoue et al., *Nucleic Acids Res.* 1987, 15, 6131–6148, and is incorporated by reference herin in its entirety) (1.6 g, 4.36 mmol) was dissolved in dry pyridine (25 mL) and the solution was cooled to 0° C. while protected from moisture. p-Toluenesulfonyl chloride (1.0 g, 5.23 mmol) was added and the reaction mixture was left at 0–3° C. for 48 h. MeOH (10 mL) was added and the mixture evaporated to a syrup. After standard work up and column chromatography using 1–2% MeOH in $CH_2Cl_2$, 7 was obtained as a colorless foam, 1.06 g (47%), $^1H$ NMR δ12.25 (br s, 1H, NH), 9.55 (br s, 1H, NH), 7.83 (d, $J_{H,H}$=8.3, 2H, Ts), 7.78 (s, 1H, H8), 7.42 (d, $J_{H,H}$=8.3, 2H, Ts), 5.83 (d, $J_{1',2'}$=6.2, 1H, H1'), 4.82 (app t, $J_{2',3'}$=5.7, 1H, H2'), 4.64 (m, 1H, H3'), 4.37 (dd, $J_{5',4'}$=2.2, $J_{5',5''}$=10.3, 1H, H5'), 5.23 (dd, $J_{4',5''}$=2.9, $J_{4',3'}$=5.2, 1H, H4'), 4.29 (dd, $J_{5'',4'}$=2.9, $J_{5'',5'}$=10.3, 1H, H5''), 3.47 (s, 3H), OMe), 2.76 (m, 1H, $CH(CH_3)_2$), 2.51 (s, 3H, Ts-Me),1.29 (m, 6H, 2×Me).

The 3',5'-Di-O-p-toluenesulfonyl derivative was also isolated (0.45 g, 15%) from the reaction mixture along with 20% of the unreacted starting material.

As shown in FIG. 8B 5'-Azido-5'-deoxy-N²-isobutyryl-2'-O-methylguanosine (8). 7 (780 mg, 1.5 mmol) was dissolved in dry DMSO (7 mL) and $LiN_3$ (370 mg, 7.56 mmol) was added under argon. The mixture was heated at 50° C. for 16 h and then evaporated to a syrup (oil pump, 50° C.). The residue was partitioned between water (30 mL) and EtOAc (30 mL). The aqueous layer was extracted with EtOAc (4×20 mL), organic layers combined, dried ($Na_2SO_4$) and evaporated to dryness. Flash column silica gel chromatography using 2–25% MeOH in $CH_2Cl_2$ afforded 8, 430 mg (78%), mp 107–109° C. ($H_2O$), $^1H$ NMR (dmso-$d_6$) δ12.17 (br s, 1H, NH), 11.68 (brs, 1H, NH), 8.36 (s, 1H, H8), 6.01 (d, $J_{1',2'}$=6.1, 1H, H1'), 5.52 (d, $J_{OH,3'}$=5.1, 1H, 3'OH), 4.47 (app t, $J_{2',3'}$=5.5, 1H, H2'), 4.37 (m, 1H, H3'), 4.12 (m, 1H, H4'), 3.75 (dd, $J_{5',4'}$=6.8, $J_{5',5''}$=13.2, 1H, H5'), 3.65 (dd, $J_{5'',4'}$=4.2, $J_{5'',5'}$=13.2, 1H, H5''), 3.43 (s, 3H, OMe), 2.86 (m, 1H, $CH/(CH_3)_2$), 1.22 (s, 3H, Me), 1.20 (s, 3H, Me).

5'-Amino-5'-deoxy-N²-isobutyryl-2'-O-methylguanosine (9) (FIG. 8B) To the solution of 8 (350 mg, 0.95 mmol) in 96% EtOH (30 mL) 10% Pd/C catalyst (60 mg) was added. The mixture was hydrogenated under 35 psi of $H_2$ for 24 h. More EtOH was added and heated to get the partly crystallized product completely into solution. Then the catalyst was filtered off. On cooling, crystals formed which were filtered off and dried to give 260 mg in two crops (80%), mp 197–199° C., $^1H$ NMR ($D_2O$) δ8.16 (s, 1H, H8), 6.15 (d, $J_{1',2'}$=4.6, 1H, H1'), 4.66 (app t, $J_{3',2'}$=5.4, $J_{3',4'}$=5.4, 1H, H3'), 4.57 (app t, $J_{2',1'}$=4.6, $J_{2',3'}$=5.4, 1H, H2'), 4.34 (m, 1H, H4'), 3.50 (s, 3H, OMe), 3.49 (m, 2H, H5', H5''), 2.82 (m, 1H, $CH(CH_3)_2$), 1.26 (s, 3H, Me), 1.24 (s, 3H, Me).

5'-N-(4-Methoxytrityl)amino-5'-deoxy-N²-isobutyryl-2'-O-methylguanosine (10) was synthesized from 9 using 4-methoxytrityl chloride/DMAP/$Et_3N$/Pyr (FIG. 8B) according to the procedure of Mag and Engels, supra, in 80% yield. $^1H$ NMR δ12.11 (br s, 1H, NH), 7.95 (br s, 1H, NH), 7.70 (s, 1H, H8), 7.53–6.86 (m, 14H, aromatic), 5.92 (d, $J_{1',2'}$=4.9, 1H, H1'), 4.55 (app t, $J_{3',4'}$=5.0, 1H, H3'), 4.35 (app t, $J_{2',1'}$=4.9, 1H, H2'), 3.84 (s, 3H, Tr-OMe), 3.55 (s, 3H, OMe), 2.82 (br s, 1H, 3'OH), 2.78 (dd, $J_{5',4'}$=3.0, $J_{5',5''}$=12.4, 1H, H5'), 2.65 (br s, 1H, NH), 2.43 (dd, $J_{5'',4'}$=5.4, $J_{5'',5'}$=12.4, 1H, H5''), 1.09 (m, 6H, 2×Me).

5'-N-(4-Methoxytrityl)amino-5'-deoxy-N²-isobutyryl-2'-O-methylguanosine-3'-O-(2-cyanoethyl-N,N-diisopropylphosphoramidite) (11). Using the same procedure as for the preparation of 5, phosphoramidite 11 was obtained (FIG. 8B) as a colorless foam in 80% yield after column chromatography using 1% EtOH in $CH_2Cl_2$ (1% $Et_3N$), $^{31}P$ NMR δ148.74 (s) and 148.06 (s).

Figure 3:
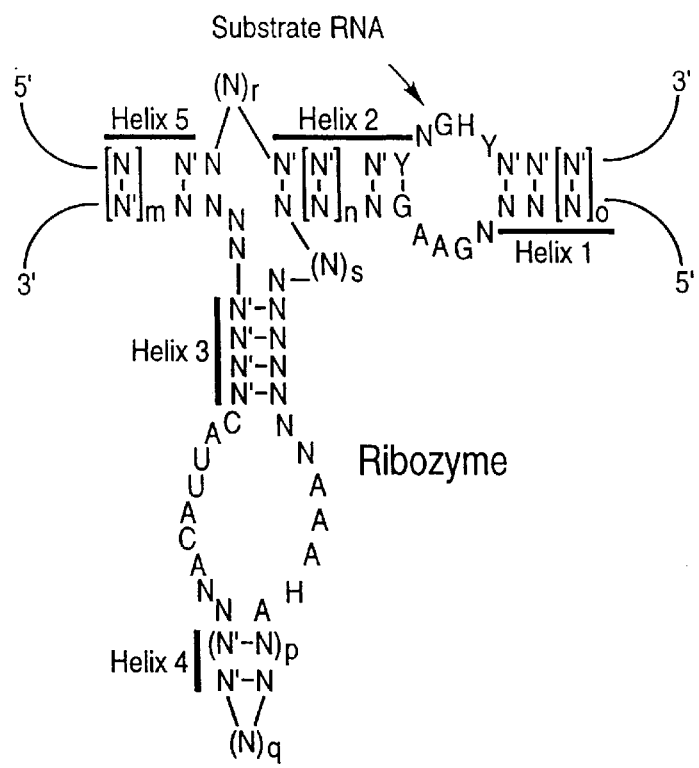

Referring to FIG. 8C, 3'-O-t-Butyldiphenylsilyl-N⁶-benzoyl-2'-O-methyladenosine (13). 5'-O(4,4'-Dimethoxytrityl)-N⁶-benzoyl-2'-O-methyladenosine 12 (5 g, 7.3 mmol) was dissolved in DMF (20 mL) and imidazole (1.5 g, 22 mmol) and t-butyldiphenylsilyl chloride (2.8 mL, 10.8 mmol) were added. The mixture was stirred at rt overnight. Methanol (10 mL) was added and the solution evaporated to a syrup. After standard work up the resulting syrup was dissolved in $CH_2Cl_2$ (100 mL) and cooled in an ice-bath. 3% TFA in $CH_2Cl_2$ (v/v, 100 mL) was added and the mixture was stirred at 0° C. for 10 min. Methanol (20 mL) and toluene (50 mL) were added and the solution concentrated to a syrup in vacuo (40° C.). The residue was coevaporated twice with toluene and then purified by column chromatography using 1–5% MeOH in $CH_2Cl_2$ for elution to yield 13 as a white foam (4.3 g, 95% yield), $^1H$ NMR δ8.98 (br s, 1H, NH), 8.73 (s, 1H, H2), 8.13 (s, 1H, H8), 8.02–7.39 (m, 15H, 3×Ph), 6.06 (d, $J_{1',2'}$=7.4, 1H, H1'), 5.86 (d, $J_{OH,5'}$=10.2, 1H, 5'OH), 4.55 (m, 2H, H2',H3'), 4.20 (br s, 1H, H4'), 3.70 (d, $J_{5',5''}$=12.9, 1H, H5'), 3.14 (d, $J_{5'',5'}$=12.9, 1H, H5''), 3.10 (s, 3H, OMe), 1.15 (s, 9H, t-Bu).

5'-O-(4-Nitrobenzenesulfonyl)-3'-O-t-butyldiphenylsilyl-N⁶-benzoyl-2'-O-methyladenosine (14) and 5'-chloro-5'deoxy-3'-O-t-butyldiphenylsilyl-N⁶-benzoyl-2'-O-methyladenosine (15). (see FIG. 8C). To a solution of 13 (4.3 g, 6.9 mmol) in dry pyridine (70 mL) was added 4-nitrobenzenesulfonyl chloride (2.47 g, 11 mmol) and the solution was left at rt overnight. Water (2 mL) was added and the solution concentrated to a syrup in vacuo. After standard work up the reaction mixture was purified by column chromatography using 1–5% gradient MeOH in $CH_2Cl_2$ to yield 4.7 g of the inseparable mixture of 14 and 15 in 2:1 ratio, $^1H$ NMR for 14 δ8.89 (brs, 1H, NH), 8.58 (s, 1H, H2), 8.16–7.36 (m, 20H, H8, aromatic), 6.00 (d, $J_{1',2'}$=3.8, 1H, H1'), 4.56 (app t, $J_{3',4'}$=5.1, 1H, H3'), 4.33 (m, 1H, H4'), 4.27 (dd, $J_{5',4'}$=2.8, $J_{5',5''}$=11.2, 1H, H5'), 4.14 (dd, $J_{5'',4'}$=5.3, $J_{5'',5'}$=11.2, 1H, H5''), 4.09 (app t, $J_{2',1'}$=3.8, 1H, H2'), 3.20 (s, 3H, OMe), 1.11 (s, 9H, t-Bu), $^1H$ NMR for 15 δ8.92 (br s, 1H, NH), 8.71 (s, 1H, H2), 8.16–7.36 (m, 20H, H8, aromatic), 6.15 (d, $J_{1',2'}$=3.9, 1H, H1'), 4.51 (app t, $J_{3',4'}$=5.1, 1H, H3'), 4.42 (m, 1H, H4'), 4.06 (app t, $J_{2',1'}$=3.9, 1H, H2'), 3.82 (dd, $J_{5',4'}$=4.3, $J_{5',5''}$=12.1, 1H, H5'), 3.54 (dd, $J_{5'',4'}$=3.9, $J_{5'',5'}$=12.1, 1H, H5''), 3.25 (s, 3H, OMe), 1.13 (s, 9H, t-Bu).

5'-Azido-5'-deoxy-3'-O-t-butyldiphenylsilyl-N⁶-benzoyl-2'-O-methyladenosine (16). (FIG. 8C) The above mixture of 14 and 15 (3.9 g) was dissolved in dry DMSO (30 mL) and $LiN_3$ (1.18 g, 24 mmol) was added. The reaction mixture was stirred at 80° C. overnight, then concentrated in vacuo (oil pump). After standard work up and column chromatography using 1–2% gradient MeOH in $CH_2Cl_2$ 16 was obtained as a colorless foam (2.55 g), $^1H$ NMR δ8.92 (br s, 1H, NH), 8.72 (s, 1H, H2), 8.15 (s, 1H, H8), 8.02–7.36 (m, 15H, 3×Ph), 6.14 (d, $J_{1',2'}$=3.4, 1H, H1'), 4.44 (app t, $J_{3',4'}$=5.1, 1H, H3'), 4.27 (m, 1H, H4'), 4.01 (app t, $J_{2',1'}$=3.4, $J_{2',3'}$=4.9, 1H, H2'), 3.53 (dd, $J_{5',4'}$=3.2, $J_{5',5''}$=13.3, 1H, H5'), 3.37 (dd, $J_{5'',4'}$=4.5, $J_{5'',5'}$=13.3, 1H, H5''), 3.29 (s, 3H, OMe), 1.13 (s, 9H, t-Bu).

5'-Amino-5'-deoxy-30'-O-t-butyldiphenylsilyl-N⁶-benzoyl-2'-O-methyladenosine (17). Using the same procedure (FIG. 8B) as for the preparation guanosine analog 9, 16 (2.5 g, 3.9 mmol) was converted into 17 (2.25 g, 94%) which resisted crystallization and was used crude in the next step, $^1H$ NMR δ8.90 (br s, 1H, NH), 8.72 (s, 1H, H2), 8.23 (s, 1H, H8), 8.02–7.36 (m, 15H, aromatic), 6.13 (d, $J_{1',2'}$=4.4, 1H, H1'), 4.72 (app t, $J_{2',1'}$=4.4, $J_{2',3'}$=5.0, 1H, H2'), 4.17 (m, 2H, H3', H4'), 3.27 (s, 3H, OMe), 2.88 (dd, $J_{5',4'}$=3.2, $J_{5',5''}$=13.8, 1H, H5'), 2.65 (dd, $J_{5'',4'}$=5.0, $J_{5'',5'}$=13.8, 1H, H5''), 1.12 (s, 9H, t-Bu).

5N-(4-Methoxytrityl)amino-5'-deoxy-3'-O-t-butyldiphenylsilyl-$N^6$-benzoyl-2'-O-methyladenosine (18). (FIG. 8C) Using the same procedure as for the preparation of 10, 17 was converted into 18, which was then purified by column chromatography using 1–2% MeOH gradient in $CH_2Cl_2$, (2.37 g, 76%) as a colorless foam, $^1H$ NMR δ8.90 (br s, 1H, NH), 8.02 (s, 1H, H2), 7.95 (s, 1H, H8), 8.00–6.71 (m, 29H, 3×Ph), 6.04 (d, $J_{1',2'}$=6.4, 1H, H1'), 4.72 (app t, $J_{2',1'}$=6.4, $J_{2',3'}$=4.4, 1H, H2'), 4.65 (m, 1H, H3'), 4.33 (m, 1H, H4'), 3.80 (s, 3H, Tr-OMe), 3.20 (s, 3H, OMe), 3.03 (br s, 1H, NH), 2.26 (d, $J_{5',5''}$32 11.7, 1H, H5'), 2.15 (dd, $J_{5'',4'}$=4.3, $J_{5'',5'}$=11.7, 1H, H5''), 1.12 (s, 9H, t-Bu).

5'-N-(4-Methoxytrityl)amino-5'-deoxy-$N^6$-benzoyl-2'-O-methyladenosine (19). (FIG. 8C) To the solution of 18 (2.7 g, 3 mmol) in THF (30 mL) 1 M tetrabutylammonium fluoride (TBAF) in THF (6 mL) was added and the mixture was stirred at rt 2 h. It was then concentrated to a syrup in vacuo. After standard work up and column chromatography using 10–30% gradient THF in $CH_2Cl_2$ 19 was obtained (1.6 g, 81%) as a colorless foam, $^1H$ NMR δ8.90 (br s, 1H, NH), 8.14 (s, 1H, H2), 7.98 (s, 1H, H8), 8.02–6.79 (m, 19H, aromatic), 5.95 (d, $J_{1',2'}$=5.5, 1H, H1'), 4.91 (app t, $J_{2',1'}$=5.5, 1H, $J_{2',3'}$=5.2,H2'), 4.72 (m, 1H, H3'), 4.29 (m, 1H, H4'), 3.77 (s, 3H, Tr-OMe), 3.52 (s, 3H, OMe), 3.09 (br s, 1H, NH), 2.67 (d, $J_{OH,3'}$=3.4, 1H, OH3'), 2.60 (dd, $J_{5',5''}$=11.7, 1H, H5'), 2.15 (dd, $J_{5'',4'}$=4.3, $J_{5'',5'}$=11.7, 1H, H5''), 1.12 (s, 9H, t-Bu).

5'-N-(4-Methoxytrityl)amino-5'-deoxy-$N^6$-benzoyl-2'-O-methyladenosine-3'-O-(2-cyanoethyl-N,N-diisopropylphosphoramidite) (20). (FIG. 8C) Using the same procedure as for the preparation of 5, 19 (1 g, 1.5 mmol) was converted into 20 and after column chromatography using $CH_2Cl_2$ containing 1% $Et_3N$ (v/v) a colorless foam (0.55 g, 74%) was obtained, $^{31}P$ NMR δ151.2 (s), 151.8 (s).

Referring to FIG. 8D,5'-Deoxy-5'-iodo-2'-O-methyluridine (21). This compound was prepared from 1 using the procedure of Verheyden and Moffatt (*J. Org. Chem.*, 1970, 35, 2319, and is incorporated by reference herin in its entirety) for selective iodination of thymidine and isolated in 59% yield by column chromatography using 1–5% MeOH in $CH_2Cl_2$ for elution, $^1H$ NMR (DMSO-$d_6$) δ7.76 (d, $J_{6,5}$=8.1, 1H, H6), 5.94 (d, $J_{1',2'}$=5.4, 1H, H1'), 5.77 (d, $J_{5,6}$=8.1, 1H, H5), 5.52 (d, $J_{OH,3}$=6.0, 1H, 3'OH), 4.11 (dd, $J_{3',2'}$=5.36, $J_{3',4'}$=10.2, 1H, H3'), 4.06 (app t, $J_{2',1'}$=5.4, 1H, H2'), 3.93 (m,1H, H4'), 3.63 (dd, $J_{5',4'}$=5.4, $J_{5',5''}$=10.6, 1H, H5'), 3.49 (dd, $J_{5'',4'}$=6.9, $J_{5'',5'}$=10.6, 1H, H5''), 3.42 (s, 3H, OMe).

5'-(S-Triphenylmethyl)mercapto-5'-deoxy-2'-O-methyluridine (22). (FIG. 8D) Sodium hydride (52 mg, 2.18 mmol) was suspended in dry DMF (1 mL) under argon at 0° C., and a solution of triphenylmethyl mercaptan (606 mg, 2.19 mmol) in dry DMF (7 mL) was added. The mixture was stirred for 10 min at rt, cooled in ice and a solution of 21 (690 mg, 1.80 mmol) in dry DMF (5 mL) was added. After 3 h at room temperature (rt) solvent was removed in vacuo, the residue dissolved in $CH_2Cl_2$ and washed with 5% aqueous $Na_2S_2O_3$ and water. The organic layer was dried ($Na_2SO_4$), evaporated to dryness and chromatographed using 1–2% MeOH in $CH_2Cl_2$ for elution to afford 22 (860 mg, 68%), mp 187–188° C. (EtOH-$H_2O$), $^1H$ NMR δ8.43 (brs, 1H, NH), 7.51–7.29 (m, 16H, Tr, H6), 5.87 (d, $J_{1',2'}$= 2.4, 1H, H1'), 5.78 (d, $J_{5,6}$=8.1, 1H, H5), 3.90 (m, 1H, H2'), 3.83 (m, 1H, H3'), 3.75 (dd, $J_{4',5'}$=2.4, $J_{4',3'}$=5.5, 1H, H4'), 2.81 (dd, $J_{5',4'}$=2.4, $J_{5',5''}$=13.0, 1H, H5'), 2.52 (dd, $J_{5'',4'}$=6.6, $J_{5'',5'}$=13.0, 1H, H5'').

5-(S-Triphenylmethyl)mercapto-5'-deoxy-2'-O-methyluridine-3'-O-(2-cyanoethyl-N,N-diisopropylphosphoramidite) (23) (FIG. 8D) Using the same procedure as for the preparation of 5, 3'-phosphoramidite 23 was obtained as a white foam in 88% yield after flash chromatography purification using 50–75% gradient of EtOAc in hexane (1% $Et_3N$), $^{31}P$ NMR δ149.1 (s) and 148.7 (s).

Ribozyme Synthesis and Purification

Incorporation of 5'-phosphoramidate at the 5'-end of ribozymes. Synthesis was performed as described (Wincott et al., supra, incorporated by reference herin in its entirety) with a 300 s coupling time for the 5'-amino phosphoramidites 5, 11 and 20 (FIGS. 8B & 8C). Detritylation was effected using a cycle that consisted of four 10 s pulses of TCA, each separated by 7 s wait steps, followed by 30 s of acetonitrile. This series was then repeated. Finally, the incoming phosphoramidite was coupled for 300 s to complete the synthesis. The ribozyme was base deprotected under standard conditions, however, desilylation was accomplished with TBAF in 24 h rather than HF/TEA solution.

Incorporation of 5'-amino group at the 5'-end. The synthesis cycle was modified slightly from the usual protocol. The 5'-amino phosphoramidites 5, 11 and 20 (FIGS. 8B & 8C) were coupled for 300 s. The usual capping reagent, acetic anhydride, was replaced with t-butylphenoxyacetic anhydride. All ribozymes were synthesized trityl-on. The terminal MMTr group was removed upon addition of four 10 s pulses of TCA, each separated by 7 s wait steps, followed by 30 s of acetonitrile. This series was repeated until no orange color was observed. The ribozyme was then deprotected under standard conditions. In the synthesis incorporating 5, a total of 323 AU of crude material resulted with 41.8% full length product (135 AU). The ribozyme was purifed by anion exchange HPLC to provide 48 AU of purified ribozyme. Similar recoveries were obtained with monomers 11 and 20.

Incorporation of bridging 5'-phosphorothioate at the 5'-end. The oligomers were synthesized using the 5'-thiol phosphoramidite 23 (FIG. 8D), coupled for 300 s, and the following amidite coupled for 400 s. Additionally, following the addition of the 5'-thiol amidite, capping and oxidation, the column was removed from the synthesizer. The cap and frit were removed, the support was washed out of the column and into an empty syringe with 10 mL of 200 mM $AgNO_3$ in 1:1 $CH_3CN:H_2O$. The syringe was capped, wrapped in foil and placed on a shaker for 1 h at rt. The mixture was then replaced into the column. The liquid was removed and the support was rinsed with 20 mL of 1:1 $CH_3CN:H_2O$. The support was then treated with 10 mL 50 mM DTT for 10 min at rt. The support is then washed with 20 mL $H_2O$, then 20 mL $CH_3CN$. The column was placed on the synthesizer, washed with $CH_3CN$ for 30 s then reverse flushed for 15 s, this procedure was repeated 4 times. The synthesis was then resumed, with the next phosphoramidite coupling for 400 s and the remaining phosphoramidites coupling for the standard times.

The ribozymes were deprotected with 40% aqueous methylamine for 10 min at 65° C. The silyl groups were removed with TEA/HF solution in 30 min at 65° C. and the oligonucleotides were precipitated from the solution. RPI.4705.5905 yielded 101.5 AU of crude material (half was lost during detritylation of 5'-STr) with 16.5% full length product.

Results

Synthesis of Monomer Building Blocks

The key intermediates for the synthesis of ribozymes containing bridging 5'-phosphoramidate and 5'-phosphorothioate linkages were 3'-O-phosphoramidites 5, 11, 20 and 23 synthesized according to FIG. 8.

5'-N-(4-Methoxytrityl)amino-5'-deoxy-2'-O-methyluridine monomer (5)

Uridine derivative 5 was synthesized in a way similar to that reported by Mag and Engels, supra, for the synthesis of a thymidine analog. 5'-Azido derivative 2 (FIG. 8B) was synthesized in one step from 2'-O-methyluridine (1) using the procedure of Yamamoto et al., supra. Ammonium hydroxide had to be used instead of water for the hydrolysis of intermediate 5'-phosphinimide during the conversion of 2 to 3 ((FIG. 8B)). It is well documented (Mungall et al., *J. Org. Chem.* 1975,40, 1659–1662) that nucleoside phosphinimines are relatively stable in water compared to simple alkyl azides. Protection of the 5'-$NH_2$ group of 3 with 4-methoxytrityl group, followed by standard phosphitylation afforded 3'-O-phosphoramidite 5 in good yield.

5'-N-(4-Methoxytrityl)amino-5'-deoxy-$N^2$-isobutyryl-2'-O-methylguanosine monomer (11)

Because the one-step procedure for the preparation of the 5'-azide described above does not work well for purine 2'-deoxynucleosides (Mag et al., supra), we used a two-step procedure for the introduction of the azido group into the 5'-position of $N^2$-isobutyryl-2'-O-methylguanosine (6) (FIG. 8B). Selective 5'-O-p-toluenesulfonation of 6 at 0° C. afforded the desired mono-substituted derivative 7 in 47% yield and 3',5'-bis-substituted derivative in 15% yield. Attempts to improve the yield and selectivity of this reaction by the portionwise addition of p-toluenesulfonyl chloride did not help. Displacement of the OTs group of 7 with an $N_3$ group using $LiN_3$ in DMSO proceeded smoothly to yield 8 in 78% yield. As in the case of uridine derivative 2 attempts to use triphenylphosphine in water/pyridine for reduction of 8 to 9 and thus avoid the simultaneous cleavage of the base labile $N^2$-isobutyryl group failed to hydrolyze the intermediate 5'-phosphinimine. Thus, catalytic hydrogenation of 8 using 10% Pd-C was utilized for the successful preparation of 5'-amino-5'-deoxy-2'-O-methyl derivative 9 (80% yield). It is worth noting that 9 underwent a gradual loss of the $N^2$-isobutyryl group when left in unbuffered aqueous solution for 16 h or longer. We attributed this unexpected deacylation to intramolecular base catalysis by the 5'-amino group of 9. Protection of the free amino group of 9 with a 4-methoxytrityl group, followed by phosphitylation afforded 3'-O-phosphoramidite 11 in a good yield.

5'-N-(4-Methoxytrityl)amino-5'-deoxy-$N^6$-benzoyl-2'-O-methyladenosine monomer (20)

The low selectivity in the tosylation of guanosine derivative 6 prompted us to to use 3'-hydroxyl protection in the preparation of adenosine analog. Thus, 5'-O-DMT derivative 12 was converted to 3'-O-TBDPSi derivative which was 5'-deprotected to yield 13 with TFA in $CH_2Cl_2$. The reaction of 13 with a more reactive sulfonylating agent, p-nitrobenzenesulfonyl chloride, yielded unexpectedly a 2:1 mixture of 5'-O-p-nitrobenzenesulfonyl and 5'-chloro-5'-deoxy substituted derivatives 14 and 15. The mixture was treated with $LiN_3$ at 80° C. overnight to afford 5'-azido-5'-deoxy derivative 16 in good yield. Catalytic hydrogenation of 16 proceeded smoothly to afford 5'-amino derivative 17 which was, without purification converted to 5'-N-MMTr protected derivative 18. Cleavage of the 3'-O-TBDPSi group was achieved using tetrabutylammonium fluoride and the resulting 19 was phosphitylated under standard conditions to give the 3'-O-phosphoramidite 20 in 74% yield (FIG. 8C).

5'-deoxy-5'-mercapto-2'-O-methyluridine monomer (23)

Synthesis of the 5'-deoxy-5'-mercapto-2'-O-methyluridine monomer 23 started with selective iodination of 2'-O-methyluridine (1) using methyltriphenoxyphosphonium iodide as described (Verheyden and Moffat, *J. Org. Chem.* 1970, 35, 2319–2326 and is incorporated by reference herin in its entirety). The iodo compound 21 was converted in 68% yield into the 5'-(S-triphenylmethyl) mercapto compound 22 using the sodium salt of triphenylmethyl mercaptan in DMF as described by Sproat et al., (*Nucleic Acids Res.* 1987, 15, 4837–4848 and is incorporated by reference herin in its entirety). Introduction of an aqueous $Na_2S_2O_3$ wash into the work up step was beneficial in reducing the cleavage of STr group and formation of intermolecular disulfide bonds by any iodine present in the reaction mixture (Kamber, *Helv. Chim. Acta* 1971,54, 398–422) Phosphitylation of 22 under standard conditions (Atkinson, T., Smith, M. *In Oligonucleotide Synthesis: A Practical Approach*, Gait, M. J., Ed.; IRL Press: Oxford, 1984, pp 35–81, and is incorporated by reference herin in its entirety) yielded 3'-O-phosphoramidite 23 (FIG. 8D).

Oligonucleotide Synthesis

Synthesis of Oligomers with Bridging 5'-Phosphoramidate

There are four issues that must be addressed when synthesizing oligomers containing bridging 5'-phosphoramidate linkages:

1. Coupling of the 5'-amine containing phosphoramidite to the growing chain; 2. Coupling of the following amidite to the 5'-amine; 3. Deprotection conditions; 4. Removal of the MMT protecting group from the 5'-amine.

After an extensive study on incorporation of 5'-amino modified monomers into ribozymes (see Table VI), we found that a coupling time of 300 s for 5 and 300 s for the following 2'-O-Me nucleotide provided the best results. For optimal results, the oligomer was desilylated with TBAF rather then HF/TEA solution as more full length polymer was produced with the former reagent.

We devised an experiment to study the influence of extended exposure of the modified oligonucleotides to the detritylation solution ($TCA/CH_2Cl_2$) and activator (tetrazole). Following completion of the synthesis, we exposed one oligomer to four "dummy cycles" of detritylation solution and another to four "dummy cycles" of activator. Although no impact upon full length product was observed with the extended detritylation exposure, there did appear to be a detrimental effect to extended exposure to activator.

Finally we investigated the removal of the MMT protecting group. The optimal procedure for removal of the MMT group required a "flow through" process. Therefore, detritylation was effected using four 10 s pulses of TCA with 7 s wait steps between each pulse. This was followed by 30 s of acetonitrile and then the four 10 s pulses of TCA were repeated. The incoming amidite was then coupled for 300 s to complete the synthesis.

Synthesis of oligomers with 5'-amino group at the 5'-end:

In the process of synthesizing ribozymes containing phosphoramidate linkages at the 5'-end, we also synthesized ribozymes that contained 5'-amines at the 5'-terminus of the ribozyme. The standard synthetic protocols were modified slightly to optimize synthesis. To ensure complete removal of the more stable MMTr protecting group on the 5'-amine, the final detritylation step was adjusted as in the previous example. In addition, t-butylphenoxyacetic anhydride was used as the capping reagent. We had observed the formation of a side product, identified by MALDI-TOF MS as the N-acetylated ribozyme, when acetic anhydride was the capping agent.

Synthesis of oligomers with bridging 5'-phosphorothioates:

A single bridging 5'-phosphorothioate linkage was incorporated into the 5'-end of two ribozymes. The 5'-thiol phosphoramidite 23 was coupled for 300 s and the following phosphoramidite coupled for 400 s. The ribozymes were base deprotected as usual and then treated with TEA/HF at 65° C. for 0.5 h rather than 1.5 h. Using the latter reagent we have not observed substantial cleavage of the P—S bond as observed when TBAF was used (Sund et al., supra).

Ribozymes containing 5'-amine at the 5'-end showed resistance to digestion by calf spleen 5'-exonuclease equivalent to that observed with P=S backbone modifications. Also, their catalytic activity was comparable to the wild type ribozymes as described infra.

Example 3

Nuclease Stability. In vitro Activity and Cell Culture Efficacy of 5'-amino-modified Ribozymes Materials and Methods Radio-labeling of Ribozymes and Substrates. Ribozymes and substrates were 5'-end-labeled using T4 Polynucleotide Kinase and $\gamma$-$^{32}$P-ATP. For internal labeling, ribozymes were synthesized in two halves with the junction 5' to the GAAA sequence in Loop II (FIG. 6). The 3'-half-ribozyme portion was 5'-end-labeled using T4 Polynucleotide Kinase and $\gamma$-$^{32}$P-ATP, and was then ligated to the 5'-half-ribozyme portion using T4 RNA ligase. Labeled ribozymes were isolated from half-ribozymes and unincorporated label by gel electrophoresis.

Ribozyme Activity Assay. Ribozymes and 5'-$^{32}$P-end-labeled substrate were heated separately in reaction buffer (50 mM Tris-HCl, pH 7.5; 10 mM MgCl$_2$) to 95° C. for 2 min, quenched on ice, and equilibrated to the final reaction temperature (37° C.) prior to starting the reactions. Reactions were carried out in enzyme excess, and were started by mixing ~1 nM substrate with the indicated amounts of ribozyme (50 nM-1 μM) to a final volume of 50 μL. Aliquots of 5 μL were removed at 1, 5, 15, 30, 60 and 120 min, quenched in formamide loading buffer, and loaded onto 15% polyacrylamide/8 M Urea gels. The fraction of substrate and product present at each time point was determined by quantitation of scanned images from a Molecular Dynamics PhosphorImager. Ribozyme cleavage rates were calculated from plots of the fraction of substrate remaining vs time using a double exponential curve fit (Kaleidagraph, Synergy Software). The fast portion of the curve was generally 60–90% of the total reaction, so that observed cleavage rates ($k_{obs}$) were taken from fits of the first exponential.

Enzymes. Calf Spleen 5'-exonuclease was purchased from Boehringer Mannheim. T4 polynucleotide kinase and Lambda 5'-exonuclease were purchased from GIBCO/BRL. Enzyme reactions were performed according to the manufacturers' suggestions.

Cell Culture. Rat aortic smooth muscle cells (SMC) were isolated from aortic tissue explants from 69–84 day-old female Sprague-Dawley rats (Harlan Sprague Dawley, Inc.) and assayed through passage six. SMC were grown in Dulbecco's modified Eagle's Medium (DMEM) supplemented with nonessential amino acids (0.1 mM of each amino acid), 0.1 mM sodium pyruvate, 100 U/mL penicillin, 100 μg/mL streptomycin, 2 mM L-glutamine, 20 mM HEPES (all from BioWhittaker) and 10% fetal bovine serum (FBS; Hyclone Laboratories, Inc.).

Preparation of Smooth Muscle Cell Extracts. Rat smooth muscle cell nuclear or total cell extracts were prepared by harvesting SMC from 3 confluent T150 flasks. For nuclear lysates, SMC were trypsinized from the flasks, washed twice with PBS, and resuspended in 500 μL of hypotonic buffer. After 40 strokes with a Dounce B homogenizer, 300 μL of 34% sucrose was added and nuclei were pelleted by centrifugation at 4° C. and 500×g for 10 min. The nuclei were washed with a solution containing 500 μL of hypotonic buffer and 300 μL of 34% sucrose, then repelleted. The pellet was resuspended in buffer A (10 mM Tris-HCl, pH 7.5; 400 mM NaCl; 1.5 mM MgCl$_2$, 0.1 mM EGTA, 5% glycerol, 0.5 mM DTT, and 0.5 mM PMSF) and given 20 strokes in the Dounce B homogenizer. The resultant suspension was gently shaken for 30 min at 4° C. and then dialyzed at 4° C. for 4 h against 100 mL of dialysis buffer (20 mM Tris-HCl, pH 7.5; 0.1 mM EDTA, 75 mM NaCl, 20% glycerol, 0.5 mM DTT and 0.5 mM PMSF). After dialysis, the solution was centrifuged at 4° C. and 16000×g for 30 min. Aliquots of the supernatant were frozen on dry ice and stored at −70° C. Separate aliquots were used for each assay.

Total cell lysates were prepared by rinsing trypsinized cell preparations 3× in PBS and pelleting by centrifugation. The pellets were resuspended in 1 mL of DMEM, 0.5 mM PMSF. PMSF was added as a precaution to minimize proteolytic activity during isolation. Cells were freeze-thawed 3 times and disrupted by 40 strokes in a Dounce B homogenizer. Aliquots of whole cell lysates were aliquoted and frozen at −70° C. Separate aliquots were used for each assay.

Ribozyme Stability Assay. One half pmol of gel-purified, internally labeled ribozyme was added to 20 μL of reaction buffer (67 mM glycine-KOH [pH 9.4], 2.5 mM MgCl$_2$, and 50 μg/mL BSA; containing either 1 μL of calf spleen 5'-exonuclease [2 U/2 mg/mL] or 10 μL of smooth muscle cell lysate). Samples were placed at 37° C. and 3 μL aliquots were withdrawn at 0, 30, 60, 120 and 240 min, and 24 h. Aliquots were quenched by the addition of 12 μL of 95% formamide, 0.5×TBE (50 mM Tris, 50 mM Borate, 1 mM EDTA) and were frozen prior to gel loading. Ribozyme integrity was assessed using electrophoresis in 12% acrylamide/7M urea gels. Undigested ribozyme samples were used as size controls. Gels. were imaged by autoradiography.

Proliferation Assays. Cells were plated in growth medium in 24-well plates at 5×10$^3$ cells per well. After 24 hours, the medium was removed, cells were washed twice with PBS containing Ca$^{2+}$/Mg$^{2+}$, and starvation medium was added. Starvation medium is growth medium in which the concentration of FBS is reduced to 0.5%. Cells were starved for 68–72 hours before ribozyme treatment. Ribozymes were diluted in serum-free DMEM with additives as above excluding antibiotics. LipofectAMINE (Gibco-BRL) was added to a final concentration of 3.6 μM DOSPA (=7.2 μg/mL LipofectAMINE). Lipid/ribozyme mixtures were vortexed, incubated for 15 minutes, and then added to cells which had been washed twice with PBS containing Ca$^{2+}$/Mg$^{2+}$. Cells were incubated with the ribozyme/lipid complexes at 37° C. for 4 hours before the mixture was aspirated away. Cells were stimulated by the addition of growth medium. Control cells were treated with lipid only and stimulated with growth medium containing either 10% or 0% FBS. All conditions were run in triplicate. At the time of stimulation, 5'-bromo-2'-deoxyuridine (BrdU, Sigma) was added at a final concentration of 10 μM. Cells were incubated for 24 h and then fixed by the addition of cold 100% methanol plus 0.3% hydrogen peroxide for 30 min at 4° C. The following reagents were used at room temperature, unless otherwise noted, to stain the BrdU containing nuclei: i) 2 M HCl for 20 minutes; ii) 1% horse serum in PBS overnight at 4° C.; iii) anti-BrdU monoclonal antibody (Becton-Dickinson) diluted 1:200 in 1% bovine serum albumin and 0.5% Tween 20 for 1 hour; iv) biotinylated horse anti-mouse IgG in DPBS for 30 minutes; v) ABC Reagent (Pierce mouse IgG kit) in DPBS for 40 minutes; vi) DAB substrate (Pierce) diluted 1:10 in DAB buffer (Pierce) for 7–10 minutes; and vii) hemotoxylin (Fisher) diluted 1:1 in deionized water for 1–2 minutes. A minimum of 500 cells per well were counted under the microscope and the percentage of proliferating cells (BrdU-stained nuclei/total nuclei) was determined.

Resistance of 5'-amino-modified Ribozymes to Digestion by Calf Spleen 5'-exonuclease Internally-labeled ribozymes were prepared by the separate synthesis of 5'-and 3'-half ribozymes, $^{32}$P end-labelling of the 3'-half ribozyme at the 5'-terminus and subsequent ligation of appropriate 5'- and 3'-half ribozymes to produce a full-length ribozyme with an internal $^{32}$P label. For stabilization against digestion by 3'-exonuclease, the 3'-ends of all ribozymes were capped with a 3'-3' linked abasic residue (FIG. 11B; Beigelman et al., 1995 supra). Unless otherwise noted, nonessential residues contained 2'-O-Me modifications, while essential residues contained 2'-ribose moieties as illustrated in FIG. 6. Modifications to ribozymes at positions 2.1–2.7 and substitutions at positions U4 and U7 are summarized in Table II. While ribozymes containing either ribose (Rz 1) or deoxyribose (Rz 2) moieties at positions 2.1–2.7 were rapidly digested by calf spleen 5'-exonuclease, ribose containing ribozymes appeared to be more resistant to digestion. 2'-O-Me modification at positions 2.1–2.7 (Rz 3) slowed digestion but did not prevent nucleolytic loss of the Stem I region after extended incubation with calf spleen exonuclease. Analysis of the digestion patterns revealed that progressive exonucleolytic digestion within each of these ribozymes stopped near the U4-amino modified residues. Identification of the U4 position as the limiting site for exonuclease digestion was achieved by counting down the digestion ladders of Rzs 1 and 2 on a gel.

Ribozymes containing partial P=S backbone (positions 2.1–2.7, Rz 4) or 5'-amino (Rz 6) modifications were resistant to digestion by exonuclease even after a 24 h incubation with the calf spleen enzyme. Although the data discussed used ribozymes containing U4/U7 amino substitutions, we found that U4-C-allyl modified ribozymes with similar P=S or 5'-amino modifications were also stable to 5'-exonucleolytic attack (e.g., Rz 8). A low level of contaminating endonuclease activity was observed in these assays and accounts for the decreased amounts of full-length P=S or 5'-amino modified ribozymes after 24 h of incubation. Similar patterns of nuclease resistance were observed for these ribozymes in parallel assays using Lambda 5'-exonuclease.

Ribozyme Stability in Rat Smooth Muscle Cell Lysates

Internally-labeled ribozymes were prepared for lysate stability assays as described in the previous section and in Materials and Methods. The 3'-ends of all ribozymes contained a 3'-3' linked abasic residue. Ribose and 2'-O-Me substitutions into the ribozyme used standard patterns which were discussed above. Modifications to positions 2.1–2.7 and 5'-end substitution for the ribozymes are summarized in Table II. The data show that ribozymes containing unprotected ribose (Rz 1) or deoxyribose (Rz 2) residues in positions 2.1–2.7 are digested in both nuclear and whole cell lysates, but at a much slower rate than was observed in assays containing purified calf spleen 5'-exonuclease. Incubation of these ribozymes in SMC lysates resulted in the progressive shortening of ribozyme fragments over time, suggesting that the molecules were being digested by a cellular 5'-exonuclease activity. While progressive 3'-end digestion by an uncharacterized cellular enzyme cannot be ruled out in these assays, previous results in serum and cell extracts have shown that the addition of a 3'-3' abasic residue at the 3'-terminus renders ribozymes resistant to 3'-exonucleolytic attack (Beigelman et al., 1995 supra).

Neither 2'-O-Me (Rz 3), P=S backbone (Rz 4) or 5'-amino (Rzs 6 and 8) modification of ribozymes totally protected the molecules from digestion in SMC extracts. An examination of the digestion patterns revealed that while there was no exonucleolytic cleavage of these ribozymes, they were fragmented by endonucleolytic attack. 2'-substitution for the U4/U7-amino groups of Rz 6 using U4/U7-C-allyl/O-Me groups of Rz 8 did not affect the resistance of 5'-amino containing ribozymes to exonucleolytic attack. Taken together with the data from the previous section, these data show that while 2'-O-Me modification can provide limited protection against 5'-exonucleolytic digestion in cellular extracts, 2'-O-Me substitution provides much less protection versus digestion by purified 5'-exonuclease. In contrast, P=S backbone and 5'-amino modifications prevented digestion by both purified calf spleen 5'-exonuclease and SMC 5'-exonuclease(s) but provided little added protection from endonucleolytic attack at the essential ribose residues (positions 5, 6, 8, 12 and 15.1). Based on these data and previous reports of the ability of U4/U7 modifications to restrict endonucleolytic attack at essential ribose residues (Beigelman et al., 1995 supra), we conclude that the effects of P=S and 5'-amino substitutions are confined to a very localized region at the 5'-end of the ribozyme.

The digestion profiles of ribozymes containing ribose (Rz 1) or deoxyribose (Rz 2) residues at positions 2.1–2.7 were quite different in the two SMC lysates. Although there was approximately 10 times more protein in the cellular lysates than in the nuclear lysates, this alone cannot account for the differences, because the degree of digestion for Rz 2 in cellular lysates was more than 10× greater than greater in nuclear lysates. In contrast, the degree of digestion for Rz 1 was approximately the same in both lysates at all times. These data suggest that nucleolytic digestion of ribozymes in SMC lysates is highly dependent upon the chemical nature of the ribozymes. Differences in the digestion patterns of Rz 1 and Rz 2 suggest that different enzymes may be responsible for the exonucleolytic digestion near the 5'-regions of these molecules. This differential chemical susceptibility of ribozymes to nucleolytic digestion was even more obvious when other cell lysates were used for comparison and in some cases (e.g., HL60 cell lysates) the ribose-containing Stem I regions were more susceptible to digestion than the deoxyribose-containing stems. Such comparative data show that the susceptibility of ribozymes to digestion by cellular nucleases is highly dependent upon both cell type and chemical modification to the ribozyme.

On the basis of the nuclease assays, we conclude that 1) 5'-amino modified ribozymes are as resistant to 5'-exonucleolytic digestion as thioated ribozymes, and 2) the advantage which P=S modifications give to ribozyme efficacy in cells is not just a result of their superior nuclease stability, but probably also results from intracellular localization or protein association which is mediated by the thioate moieties within the ribozymes.

Catalytic Activity of 5'-amino Modified Ribozymes

The relative effect of 5'-amino substitution on ribozyme catalytic activity was investigated under standard assay conditions as described, supra, in Materials and Methods. The catalytic activity of each ribozyme was assayed at two concentrations and the results were plotted to determine the region of the reaction which gave exponential rates at each concentration. Cleavage rates ($k_{obs}$ values) were calculated from fits of the first exponential. Table III shows an activity comparison for the five U4/U7-amino containing ribozymes at concentrations of 40 and 500 nM (roughly 4 and 50 fold above $K_M$). Activity is presented both as the cleavage rate ($min^{-1}$) and as a percentage of the rate for the control, Rz 3.

Comparison of the catalytic rates of selected ribozymes from Table II revealed that neither P=S nor 5'-amino modification of Rz 3 (Rzs 4 and 6, respectively) affected the catalytic rate significantly. Ribozymes containing 2'-O-Me substitutions at positions 2.1–2.7 (Rz 3) (FIG. 6) showed slightly better catalytic activity (20–30%) in this assay than ribozymes containing ribose moieties at these positions (Rz 1). As reported earlier (Beigelman et al., 1995 supra), we generally see very similar catalytic rates for ribozymes containing ribose and 2'-O-Me substitutions at positions 2.1–2.7 (FIG. 6) although there are generally also substitutions at positions 15.1–15.7 (FIG. 6) in the molecules which have been compared. The $k_{obs}$ values for P=S and 5'-amino modified ribozymes (Rz 4 and 6, respectively) were equivalent, within error, to those of the ribose-containing Rz 1.

The deoxyribose-substituted Rz 2 is peculiar in that it showed a 6–10 fold reduction in activity when compared with the other 2.1–2.7 position (FIG. 6) substitutions (Rzs 1, 3,4, and 6). The similarity in cleavage rates at 40 and 500 nM for this ribozyme suggest that the reduced $k_{obs}$ for Rz 2 was not a result of reduced binding affinity but more likely reflects a 6–10 fold decrease in $k_{cat}$.

This data represents the first comparative report of the effects of substitution at positions 2.1–2.7 into ribozymes using U4/U7-amino (or U4/N7-amino) stabilized ribozymes and additionally demonstrates that nuclease stabilizing modifications can be used to replace P=S backbone substitutions in ribozymes without reducing catalytic activity.

Cellular Efficacy of 5'-amino Modified Ribozymes

Based on catalytic data (Table III) and the increased stability observed with 5'-amino modified Rz 6 and 8 in the nuclease assays, we decided to compare the efficacy of Rz 6 to the thioated Rz 4 in cell assays of ribozyme activity. The relative abilities of ribozymes containing various modifications at positions 2.1–2.7 (FIG. 6) and/or the 5'-terminus were compared in a cell proliferation assay using rat smooth muscle cells. Ribozymes were delivered using lipofectAMINE as described, supra, in the Materials and Methods section. After the application of ribozymes, cells were metabolically labeled with BrdU for 24 h and the number of proliferating SMC nuclei were determined by differential staining using an anti-BrdU antibody detection system and hematoxylin.

Figure 9:
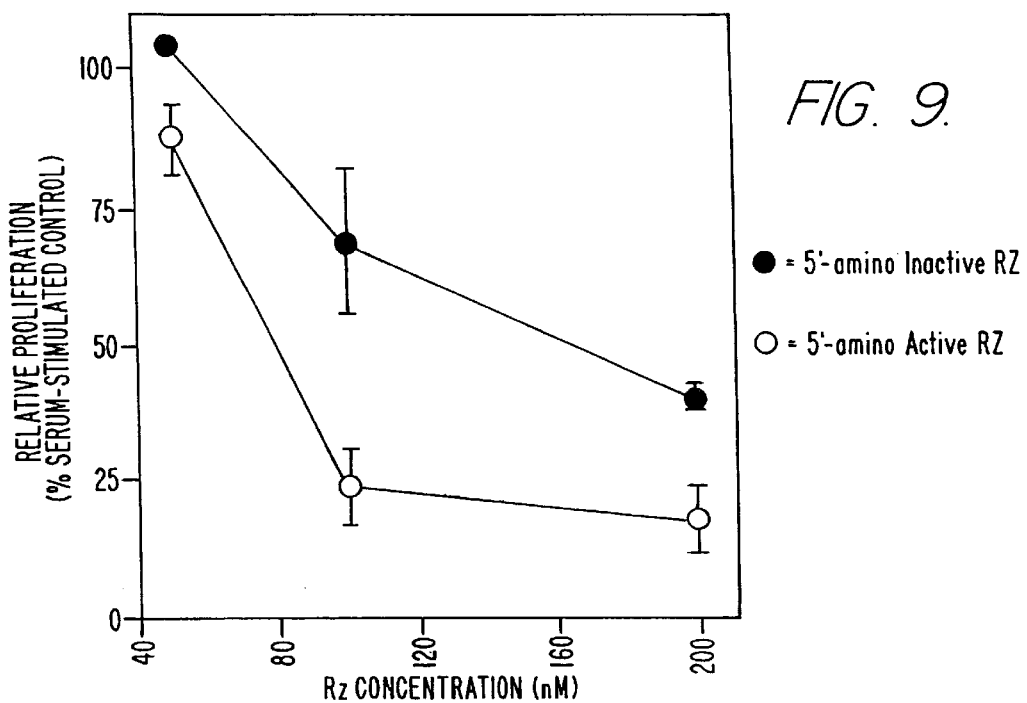

Ribozymes containing ribose (Rz 1), deoxyribose (Rz 2) or 2'-O-Me modified (Rz 3) nucleosides at positions 2.1–2.7 as well as catalytically inactive (Rzs 5, 7, 9, and 11) were included as controls for non-specific ribozyme inhibition. The stability data suggested that Rz 1 and 2 would be unstable in SMC, and previous results comparing thioated and nonthioated ribozymes suggested that even though Rz 3 is relatively nuclease-resistant in the SMC lysates, nonthioated ribozymes would be less effective in cellular assays. Ribozymes with catalytically inactivated core regions (Rz 5, 7, 9, and 11) were included to differentiate true ribozyme activity from non-specific phosphorothioate effects. Ribozymes with catalytically active cores containing either U4/U7-amino or U4/U7-C-allyl-O-Me modifications and P=S (Rz 4 and Rz 10, respectively) or 5'-amino modifications (Rz 6 and Rz 8, respectively) were included as positive controls. The relative abilities of each ribozyme to inhibit SMC proliferation are summarized in Table IV and shown graphically in FIGS. 9 and 10.

As shown in Table IV, ribozymes with ribose (Rz 1), deoxyribose (Rz 2) or 2'-O-Me (Rz 3) moieties at positions 2.1–2.7 exhibited similarly low levels of inhibitory activity in the SMC proliferation assay. The deficiency of inhibitory action by either Rz 1 or Rz 2 reflected the inherent nuclease susceptibility of these molecules in SMC lysates and suggested that even the low levels of nuclease activity which we observed in the lysates may be enough to digest unstablized ribozymes quickly within the cellular enivironment. Alternatively, Rzs 1 and 2 may be showing lower efficiency of inhibition of cellular proliferation because they are not localized near target molecules. The lower efficacy with Rz 3 is consistent with this latter hypothesis. Based upon our data showing the resistance of Rz 3 to digestion using purified preparations of calf spleen 5'-exonuclease, these molecules are expected to be relatively stable within the cells, yet they don't decrease cellular proliferative rates any better than Rzs 1 or 2. We feel that Rz 3 preparations are stable within cells and the decreased inhibitory activity may be because of issues unrelated to their nuclease susceptibility.

Comparison of the relative efficacies showed that U4/U7-amino containing 5'-amino-modified Rz 6 was as effective at inhibiting SMC proliferation as the thioate-stabilized Rz 4. Both of these molecules were more effective than the 5'-amino, U4-C-allyl modified Rz 8, which was slightly more active than Rzs 1–3. Further, Rz 6, but not Rz 4 showed better efficacy than their catalytically inactive counterparts, Rzs 7 and 5, respectively. These data show that P=S modifications of ribozymes enhance their cellular efficacy over that seen with non-stabilized ribozymes. Similar efficacies can be achieved without the apparent non-specific effects of the thioated compounds when other nuclease-stabilizing chemistries are present within the ribozyme structure (e.g., the 5'-amino modification). The further observation that nuclease-stable, Rz 5 exhibited better inhibitory activity than nuclease-sensitive, catalytically active Rzs 1 and 2 shows that nuclease stabilization is important for efficient ribozyme efficacy in cells when the ribozymes are delivered exogenously.

Figure 10:
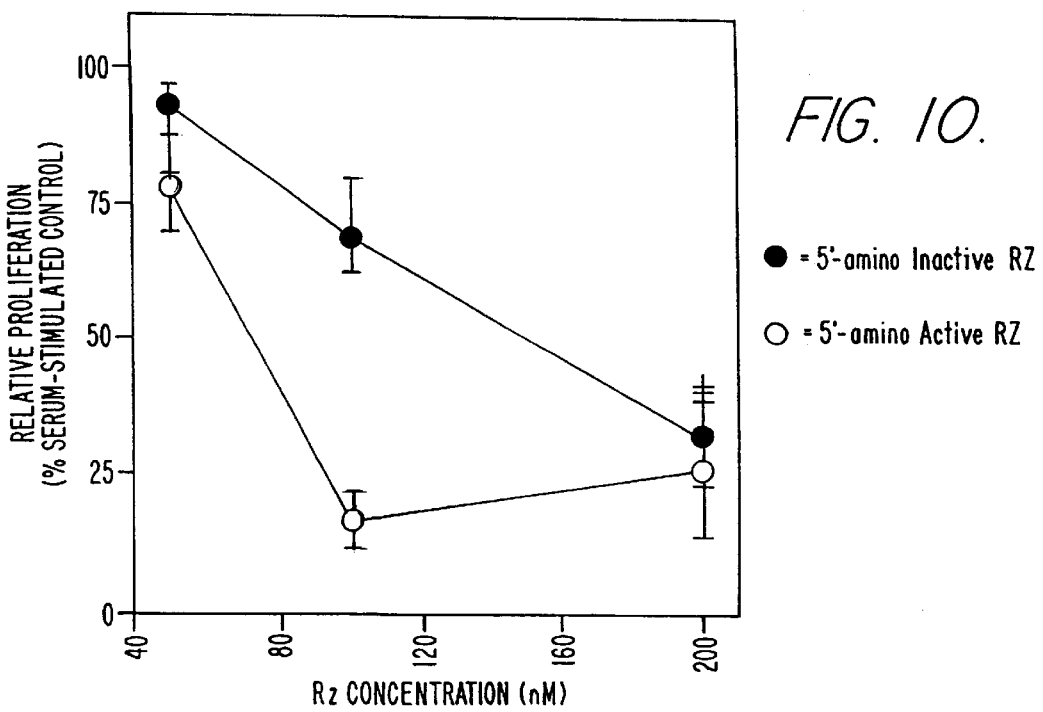

In summary, we have found that 5'-amino, U4/U7-amino modified ribozymes exhibited in vitro stability, in vitro catalytic activity and cellular efficacy (FIGS. 9 and 10) which was equivalent to similar thioated, U4/U7-amino modified ribozymes. Additionally, 5'-amino containing ribozymes showed slightly better cellular efficacy when using the U4/U7-amino format (FIG. 9, 5'-amino Active RZ) than with the U4-C-allyl format (FIG. 10, 5'-amino Active RZ). This latter observation reflected slightly better in vitro catalytic activities which were observed with the U4/U7-amino compounds.

Taken together, these data support the notion that a 5'-amino modification to ribozymes will enhance their intracellular stability and enable intracellular efficacy in a manner which is consistent with their observed relative catalytic rates in vitro. Although it is not possible to determine on the basis of these studies whether 5'-amino containing ribozymes colocalize to the same. intracellular region as thioated ribozymes, these results do suggest that 5'-amino modified ribozymes can be used effectively in animal studies of ribozyme efficacy without exhibiting some of the concentration dependent non-specific effects which have been observed by others when using thioated antisense oligonucleotides.

Example 4

Terminal Modification of Ribozymes Using Phosphorothioates

Comparison of 5'-end versus 3'-end modifications— Ribozymes targeting c-myb site 575, as described in Example in 3, supra, were complexed with LipofectAMINE and delivered to rat aortic smooth muscle cells at a 100 nM dose. Cell proliferation was measured as described in Materials and Methods of Example 3, supra. Active and inactive versions of several different chemical modifications were tested. "2'-C-Me" indicates an RNA core with five 2'-O-methyl residues at the 5'- and 3'-ends. "2'-C-Me P=S" indicates an RNA core with five 2'-O-methyl phosphorothioate residues at the 5'- and 3'-ends. "U4 C-allyl" and "U4 C-allyl P=S" indicate U4 2'-C-allyl "stabilized" cores without and with phosphorothioate linkages at the 5'- and 3'-ends, respectively. "U4,7 NH$_2$" and "U4,7 NH$_2$ P=S" indicate U4 and U7 2'-amino "stabilized" cores without and with phosphorothioate linkages at the 5'- and 3'-ends, respectively. Relative smooth muscle cell proliferation is calculated as follows: (%proliferation with ribozyme– %basal proliferation)+(%proliferation with serum–%basal proliferation)×100.

The results indicate that both a nuclease-resistant core and phosphorothioate linkages in the binding arms are necessary for significant cell culture efficacy when the ribozymes are delivered exogenously. Since phosphorothioate linkages may be associated with some degree of cytotoxicity and some non-specific effects [Uhlmann et al., 1990 Chem. Rev. 90, 543], we wished to determine the minimum number of phosphorothioates sufficient for ribozyme-mediated cell efficacy. A comparison of ribozymes containing either 5 phosphorothioate linkages at the 5'-end, or 5 phosphorothioate linkages at the 3'-end, or 5 phosphorothioate linkages at both the 5'- and 3'-ends. The ribozyme containing phosphorothioates only at the 3'-end showed only marginal efficacy when compared with an inactive ribozyme, while the ribozyme containing phosphorothioates at the 5'-end showed equivalent efficacy to that containing phosphorothioates at both the 5'- and 3'-ends. In this experiment, the inactive ribozyme showed some inhibition relative to the vehicle-treated control. A ribozyme with scrambled sequence binding arms exhibited an equivalent degree of inhibition to an inactive ribozyme, indicating that this effect was not mediated by ribozyme binding, but was truly a "non-specific" effect on proliferation. Next, we compared ribozymes with varying numbers of phosphorothioates at the 5'-end. The degree of efficacy gradually decreased as the number of phosphorothioate linkages was reduced. From these experiments we concluded that a minimum of four to five phosphorothioate linkages at the 5'-end is sufficient to maintain optimal efficacy.

The ribozymes used in this study contained either 3'-phosphorothioate linkages, or a 3'-3' "inverted thymidine" modification to protect against 3'-exonuclease activity. We have subsequently shown that the outcome of this assay is not particularly sensitive to the presence or absence of this 3'-protecting group. C-myb ribozymes containing various protecting groups including a 3'-3' inverted thymidine, a 3'-3' inverted abasic residue, a 3'-butanediol showed equivalent efficacy in inhibiting smooth muscle cell proliferation.

Example 5

Incorporation of Phosphorodithioate Linkages into Ribozymes Materials and Methods Referring to FIG. 12, 2'-O-TBDMS-5'-O-DMT-N-protected ribonucleosides, 5'-O-DMT-N-protected deoxy- and 2'-O-Me ribonucleosides were from Chem Genes Corporation, Waltham, Mass. Commercially available anhydrous solvents were employed without purification. Concentrations of solutions were carried out in vacuo at 40° C. or lower using an aspirator or an oil vacuum pump. Solids were dried at room temperature in a desiccator over phosphorus pentoxide and potassium hydroxide. $^{31}$P NMR spectra were recorded on a Varian Gemini 400 spectrometer operating at 161.947 MHz with 85% phosphoric acid as external standard. Oligonucleotides were synthesized on an Applied Biosystems 381A synthesizer using Applied Biosystems columns.

General Procedures

Ribonucleoside 3'-S-(2-cyanoethyl)N,N-dimethylthiophosphoramidite synthesis:

Suitably protected 2'-t-butyldimethylsilyl-5-O'-dimethoxytrityl nucleoside (2.0 mmol) (FIG. 12) was dried and was dissolved in dry dichloromethane (CH$_2$Cl$_2$) (20 ml) under argon and the solution was cooled to 0° C. (ice-bath). The mixture of N,N-diisopropylethylamine (DIPEA) (0.56 ml, 3.20 mmol) and N,N,N',N'-tetra- methylchlorophosphordiamidite [PCl(NMe$_2$)$_2$] (0.40 g, 2.60 mmol) in dry CH$_2$Cl$_2$ (5 ml) was added dropwise to the above solution under constant stirring. The mixture was stirred at rt for 30 min after which time β-mercaptopropionitrile (0.44 g, 5.0 mmol) was added and the reaction mixture was stirred at rt for additional 1 h. The mixture was then poured into CH$_2$Cl$_2$ (100 ml, 1% triethylamine) and washed with saturated NaHCO$_3$ (100 ml), 10% aq. Na$_2$CO$_3$ (2×100 ml) and saturated brine (100 ml). The organic layer to which 1 ml of Et$_3$N was added was dried (Na$_2$SO$_4$) for 20 min and concentrated to ca 10 ml in vacuo. This solution was added dropwise into the stirred , cooled (0° C.), degassed hexanes (200 ml, 1% Et$_3$N). The precipitate was filtered off and dried in vacuo to yield the product as a white powder.

2'-Deoxy- and 2'-O-methylribonucleoside 3'-S-(2-cyanoethyl)N,N-dimethylthiophosphoramidite synthesis:

Suitably protected 5'-O-dimethoxytrityl nucleoside (4 mmol) and DIPEA (1.05 ml, 6.0 mmol) were dried and were dissolved in dry CH$_2$Cl$_2$ (30 ml) under Ar and the solution was cooled to 0° C. (ice-bath). PCl(NMe$_2$)$_2$ (0.62 g, 4.0 mmol) was added dropwise under stirring. The clear solution was stirred at rt for 10 min, then β-mercaptopropionitrile (0.42 g, 4.8 mmol) was added and the solution was stirred at rt for additional 1 h. The work up of the reaction mixture as described for ribonucleosides above yielded products as white powders.

Synthesis with manual thiolation:

Model syntheses of ribo and 2'-O-methyl dithioate oligonucleotide sequences was performed on an ABI model 394 synthesizer using a modified synthesis cycle for thiolation. A 10 μmol cycle was created to accomodate manual sulfurization off of the instrument. This was accomplished by placing an interrupt step immediately after the phosphoramidite coupling step following the final acetonitrile wash and argon flush. The synthesizer column containing the oligo bound solid support was subsequently removed from the instrument. One frit was then removed from the end of the column and a 20 ml syringe attached to that end. At the other end of the column (the end with a frit) was attached a 20 ml syringe containing a solution of 1.5 g elemental sulfur dissolved in 20 ml of carbon disulfide and 2,6-lutidine (1:1 by volume). By forcing the thiolation solution through the column, the support was transferred to the empty syringe. This syringe, now containing the support suspended in thiolation solution, was capped off and placed on an orbital shaker for one hour. The syringe containing the suspended support was then reattached to the end of the column without a frit and the contents transferred back to the column. A new frit was then placed on the column. Excess sulfur was then washed off the support with a 20 ml solution of carbon disulfide/2,6-lutidine 1:1 followed by 20 ml anhydrous acetonitrile. Synthesis was then resumed by placing the column back on the instrument. The synthesizer cycle was resumed and the entire process repeated as necessary for each dithioate substitution introduced into the oligo. It should be noted that a 300 second coupling time was utilized for 2'-O-methyl residues while a 600 second coupling time was utilized for ribo residues. Also, the use of S-ethyl tetrazole was avoided in order to minimize side reactions resulting from the more labile dimethylamino substituted phosphoramidite moiety. Also note oxidation prior to capping in the cycle. Cleavage from the support and deprotection results from treatment of the solid support with a solution of 15% benzene or toluene in saturated ethanolic ammonia (−70° C. sat.) for 2 hours at rt and 15 hours at 55° C. Our studies demonstrate 90% thiolation efficiency under these conditions as determined by 31P NMR analysis of crude material.

Synthesis with automated thiolation:

A new synthesizer cycle (2.5 μmol) was created for fully automated synthesis of 2'-O-methyl and ribo phosphorodithioate oligonucleotides. Tetrazole was used in place of S-ethyl tetrazole to minimize side reactions. The following bottle positions on the ABI 394 synthesizer were assigned to the following solutions:

position #10: carbon disulfide:pyridine:TEA, elemental sulfur (95:95:10, 5%) Note: this solution must be used within 24 hours for optimum results.

position #15: carbon disulfide position #19: dichloromethane

The synthesis cycle was designed to deliver 12 equivalents or less of phosphoramidite with 600 second coupling times for ribo residues and 300 second coupling times for 2'-O-methyl residues. After coupling, thiolation solution (bottle #10) is delivered in two pulses. In our studies, the thiolation time was varied between 1 and 60 minutes, with an optimum time of 6 minutes. Care must be taken to avoid precipitation of sulfur in the synthesizer lines; as such, carbon disulfide (bottle #15) washes precede and follow delivery of the thiolation solution. Dichloromethane washes (bottle #19) are used to remove excess carbon disulfide from the column. In our studies, oxidation with aqueous iodine/pyridine followed standard capping in order to visualize incomplete thiolation by 31P NMR. This step was necessary for optimization, but is to be removed from standard synthetic dithioate protocols due to the increased possibility of phosphorothioate and phosphodiester contamination. Cleavage from the support and deprotection results from treatment of the solid support with a solution of 15% benzene or toluene in saturated ethanolic ammonia (−70° C. sat.) for 2 hours at rt and 15 hours at 55° C. Our studies demonstrate 90% thiolation efficiency under these conditions as determined by 31P NMR analysis of crude material.

Example 6

General Procedure for the Synthesis of Carbocyclic Nucleoside Phosphoramidites

Figure 14:
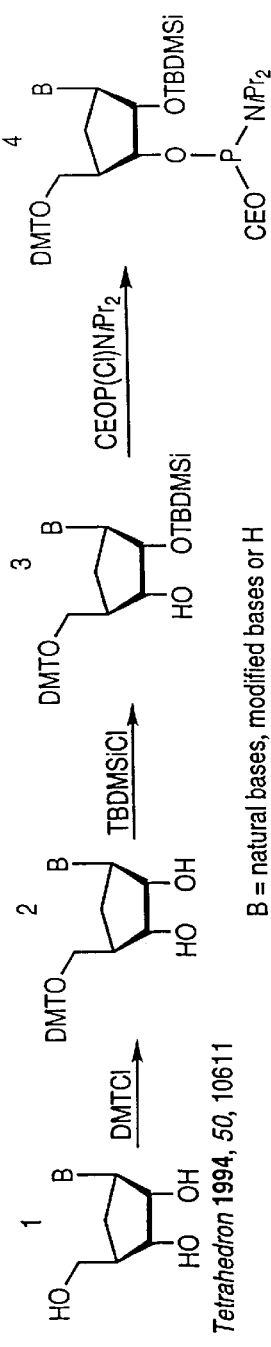
FIG. 14 is a synthesis scheme for carbocyclic nucleoside phosphoramidite.

Referring to FIG. 14, carbocyclic nucleosides (1) are synthesized essentially as described by Agrofoglio et al., 1994, *Tetrahedron* 50, 10611. Carbocyclic nucleosides (1) were 5'-protected for example by 5'-O-dimethoxytritylating 1 according to the standard procedure (see Oligonucleotide Synthesis: A Practical Approach, M. J. Gait Ed.; IRL Press, Oxford, 1984, p 27, and is incorporated by reference herin in its entirety) to yield 2 in high yield in the form of yellowish foams after silica gel column chromatography. To the stirred solution of the protected nucleoside 2 in 50 mL of dry THF and pyridine (4 eq), $AgNO_3$ (2.4 eq) was added. After 10 minutes tert-butyldimethylsilyl chloride (1.5 eq) was added and the reaction mixture was stirred at room temperature for 12 hours. The resulted suspension was filtered into 100 mL of 5% aq $NaHCO_3$. The solution was extracted with dichloromethane (2×100 mL). The combined organic layer was washed with brine, dried over $Na_2SO_4$ and evaporated. The residue containing 3 was purified by flash chromatography on silica gel. Compound 3 was then phosphitylated in the following way: To the ice-cooled stirred solution of protected nucleoside 3 (1 mmol) in dry dichloromethane (20 mL) under argon blanket was added dropwise via syringe the premixed solution of N,N-diisopropylethylamine (2.5 eq) and 2-cyanoethyl N',N-diisopropylchlorophosphoramidite (1.2 eq) in dichloromethane (3 mL). Simultaneously via another syringe N-methylimidazole (1 eq) was added and stirring was continued for 2 hours at room temperature. After that the reaction mixture was again ice-cooled and quenched with 15 ml of dry methanol. After 5 min stirring, the mixture was concentrated in vacuo (<40° C.) and purified by flash chromatography on silica gel to give corresponding phosphoroamidite 4.

Carbocyclic nucleoside phosphoramidites are incorporated into ribozymes using solid phase synthesis as described by Wincott et al., 1995 supra, incorporated by reference herein in its entirety. The ribozymes are deprotected using the standard protocol described above.

Example 7

General Procedure for the Synthesis of Alpha Nucleoside Phosphoramidites

Figure 15:
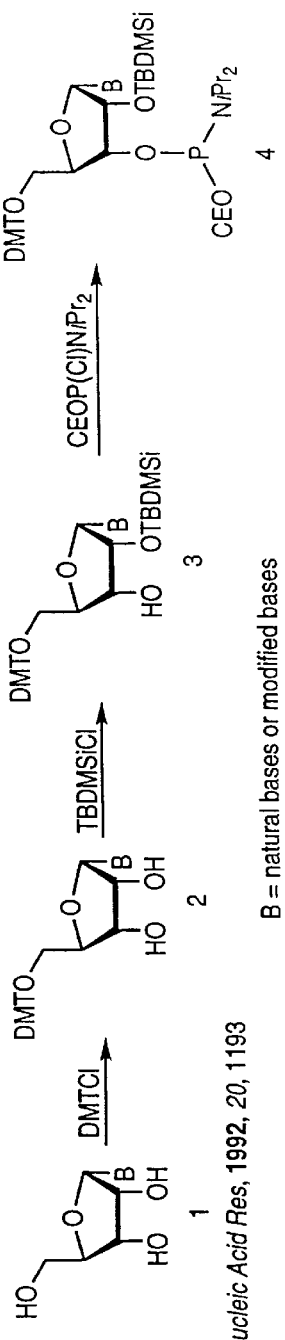
FIG. 15 is a synthesis scheme for alpha nucleoside phosphoramidite.

Referring to FIG. 15, alpha nucleosides (1) are synthesized essentially as described by Debart et al., 1992, *Nucleic Acid Res.* 20, 1193; and Debart et al. 1995, *Tetrahedron Lett.* 31, 3537. Alpha nucleosides (1) were 5'-protected for example by 5'-Odimethoxytritylating 1 according to the standard procedure (see Oligonucleotide Synthesis: A Practical Approach, M. J. Gait Ed.; IRL Press, Oxford, 1984, p 27, and is incorporated by reference herin in its entirety) to yield 2 in high yield in the form of yellowish foams after silica gel column chromatography. To the stirred solution of the protected nucleoside 2 in 50 mL of dry THF and pyridine (4 eq), $AgNO_3$ (2.4 eq) was added. After 10 minutes tert-butyldimethylsilyl chloride (1.5 eq) was added and the reaction mixture was stirred at room temperature for 12 hours. The resulted suspension was filtered into 100 mL of 5% aq $NaHCO_3$. The solution was extracted with dichloromethane (2×100 mL). The combined organic layer was washed with brine, dried over $Na_2SO_4$ and evaporated. The residue containing 3 was purified by flash chromatography on silica gel. Compound 3 was then phosphitylated in the following way: To the ice-cooled stirred solution of protected nucleoside 3 (1 mmol) in dry dichloromethane (20 mL) under argon blanket was added dropwise via syringe the premixed solution of N,N-diisopropylethylamine (2.5 eq) and 2-cyanoethyl N',N-diisopropylchlorophosphoramidite (1.2 eq) in dichloromethane (3 mL). Simultaneously via another syringe N-methylimidazole (1 eq) was added and stirring was continued for 2 hours at room temperature. After that the reaction mixture was again ice-cooled and quenched with 15 ml of dry methanol. After 5 min stirring, the mixture was concentrated in vacuo (<40° C.) and purified by flash chromatography on silica gel to give corresponding phosphoroamidite 4.

Alpha nucleoside phosphoramidites are incorporated into ribozymes using solid phase synthesis as described by Wincott et al., 1995 supra, and is incorporated by reference herin in its entirety. The ribozymes are deprotected using the standard protocol described above.

Example 8

Figure 16:
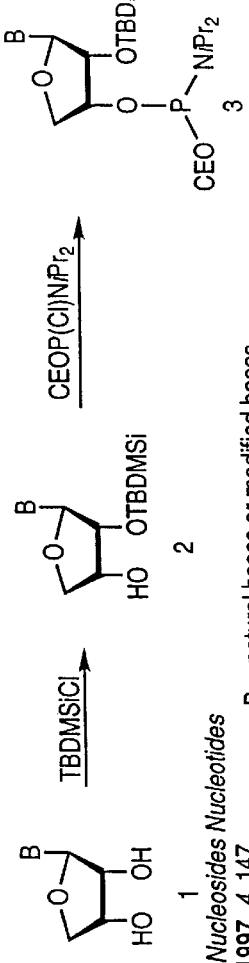
FIG. 16 is a synthesis scheme for 1-(β-D-erythrofuranosyl) nucleoside phosphoramidite.

General Procedure for the Synthesis of 1-(β-D-erythrofuranosyl) Nucleoside Phosphoramidites Referring to FIG. 16, 1-(β-D-erythrofuranosyl) nucleosides (1) are synthesized essentially as described by Szekeres et al., 1977, *J. Carbohydr. Nucleosides Nucleotides.* 4, 147. 1-(β-D-erythrofuranosyl) nucleosides (1) were treated with $AgNO_3$ (2.4 eq). After 10 minutes tert-butyldimethylsilyl chloride (1.5 eq) was added and the reaction mixture was stirred at room temperature for 12 hours. The resulted suspension was filtered into 100 mL of 5% aq $NaHCO_3$. The solution was extracted with dichloromethane (2×100 mL). The combined organic layer was washed with brine, dried over $Na_2SO_4$ and evaporated. The residue containing 2 was purified by flash chromatography on silica gel. Compound 2 was then phosphitylated in the following way: To the ice-cooled stirred solution of protected nucleoside 2 (1 mmol) in dry dichloromethane (20 mL) under argon blanket was added dropwise via syringe the premixed solution of N,N-diisopropylethylamine (2.5 eq) and 2-cyanoethyl N',N-diisopropylchlorophosphoramidite (1.2 eq) in dichloromethane (3 mL). Simultaneously via another syringe N-methylimidazole (1 eq) was added and stirring was continued for 2 hours at room temperature. After that the reaction mixture was again ice-cooled and quenched with 15 ml of dry methanol. After 5 min stirring, the mixture was concentrated in vacuo (<40° C.) and purified by flash chromatography on silica gel to give corresponding phosphoroamidite 3.

1-(β-D-erythrofuranosyl) nucleoside phosphoramidites are incorporated into ribozymes using solid phase synthesis as described by Wincott et al., 1995 supra. The ribozymes aree deprotected using the standard protocol described above.

Example 9

Figure 17:
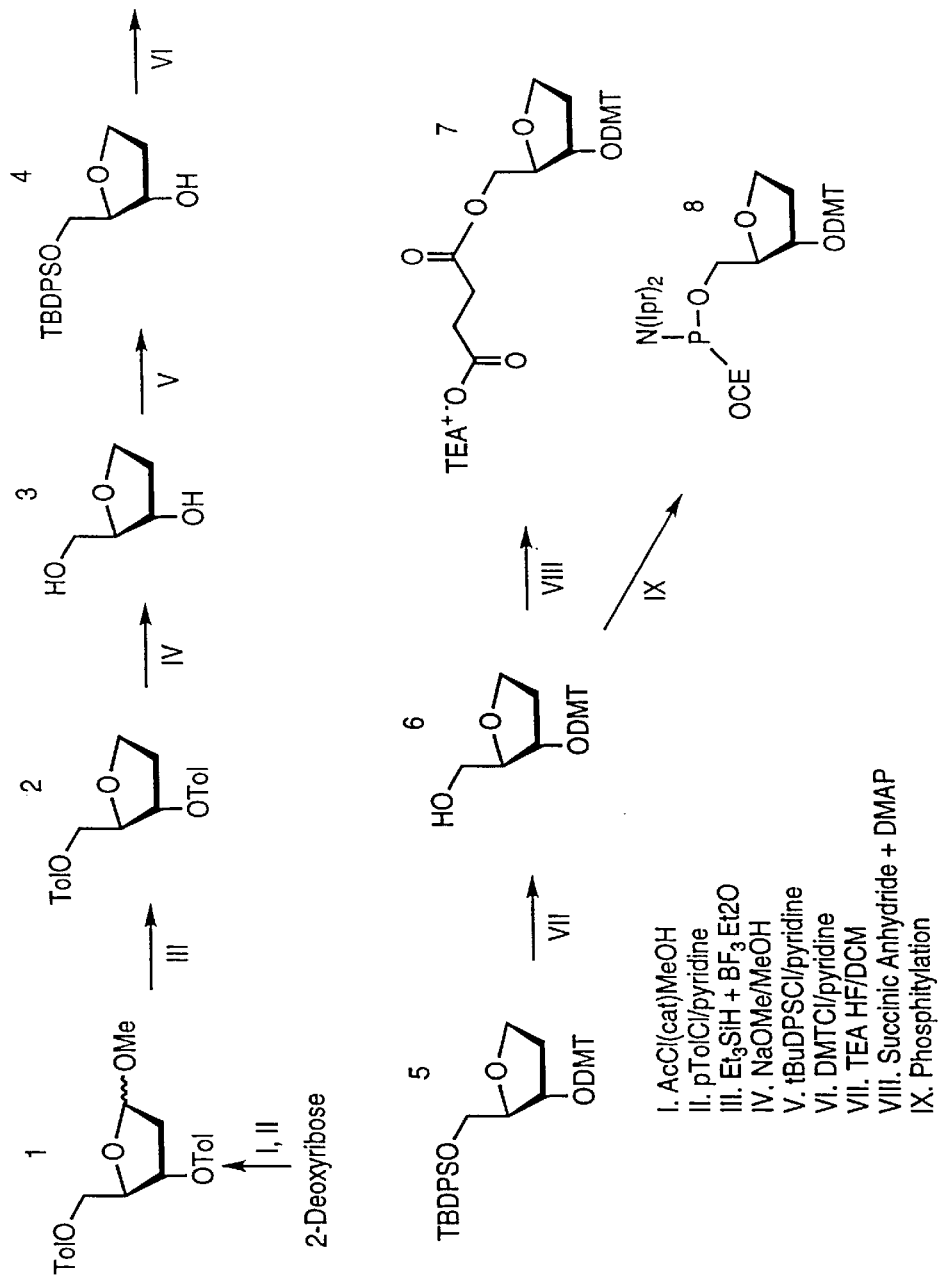
FIG. 17 is a synthesis scheme for inverted deoxyabasic 5'-O-succinate and 5'-O-phosphoramidite.

General Procedure for the Synthesis of Inverted Deoxyabasic 5'-O-Succinate and 5'-O-Phosphoramidite Referring to to FIG. 17, commercially available 2-deoxyribose is converted to compound 1 in a two step process. In the first step, 2-deoxyribose is treated with a mixture of acetyl chloride and methanol. In the second step, the reaction mixture is treated with p-toluoyl chloride/pyridine mixture to yield 1. Compund 1 is incubated with a mixture of triethyl silane and boron trifluoride in ethanol to yield compound 2. Treatment of 4 with sodium methylate in methanol yield compound 3. Reacting 3 with t-butyl-diphenyl-silyl chloride in pyridine yields compound 4. The 3'-end of 4 is tritylated using 4,4'-dimethoxytrityl chloride in pyridine to yield compound 5. The 5'-protecting group in 5 can be removed using a mixture of triethylamine/hydrogen fluoride/DCM to yield 6.

A succinate group can be attached to the 5'-end of compound 6 by reacting the compound with a mixture of succinic anhydride and 4-dimethylaminopyridine to yield compound 7.

Figure 7B:
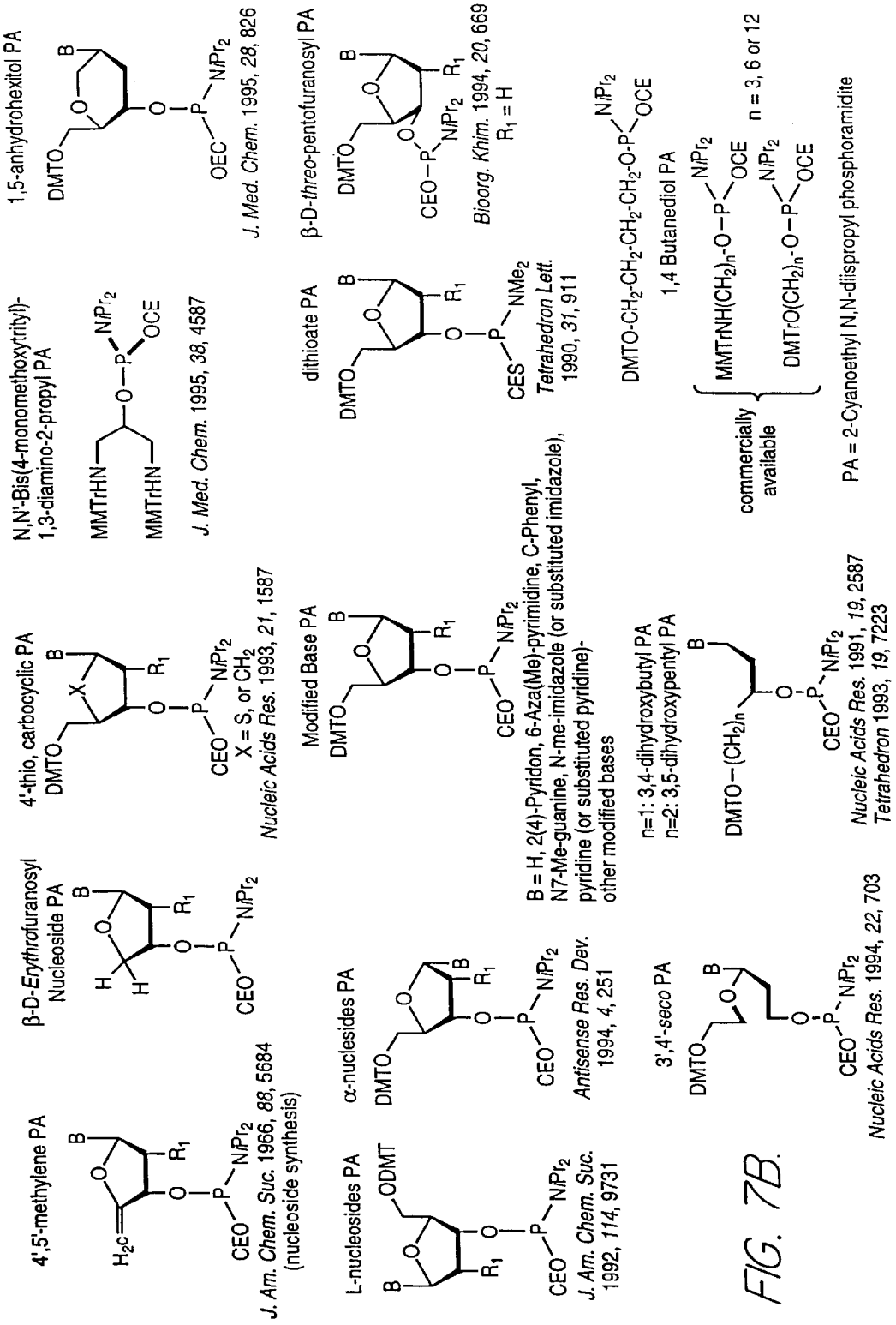
Figure 7C:
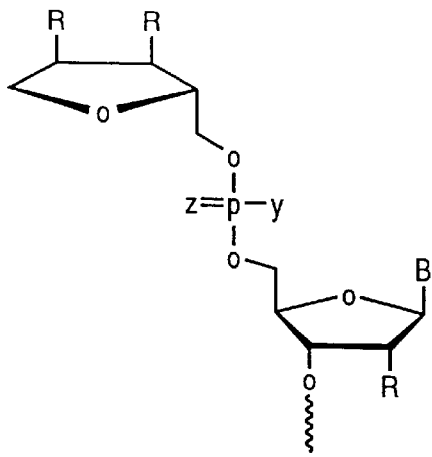

Compound 6, can be converted into a phosphoramidite by standard phosphitylation reaction described supra to yield compound 8. Reaction of 8 with a standard phosphoramidite will yield a 5'-5'-inverted abasic deoxyribose linkage as shown in FIG. 7C.

Example 10

General Procedure for the Synthesis of 3'-2'-inverted Nucleotide or 3'-2'-inverted Abasic Linkage Refering to FIG. 13, a commercially available 5'-dimethoxytrityl-3'-silyl-containing nucleoside (1) is treated with a standard phosphitylation reagent such as 2-cyanoethyl N',N-diisopropylchlorophosphoramidite to yield compound 2. Reaction of compound 3, wherein B is a natural or a modified base (described in Seliger et al., Canadian Patent Application Publication No. 2,106,819., and is incorporated by reference herein), with compound 2 will result in a 3'-2'-inverted nucleotide linkage as shown in FIG. 11B (3'-2'-inverted nucleotide).

Figure 11A:
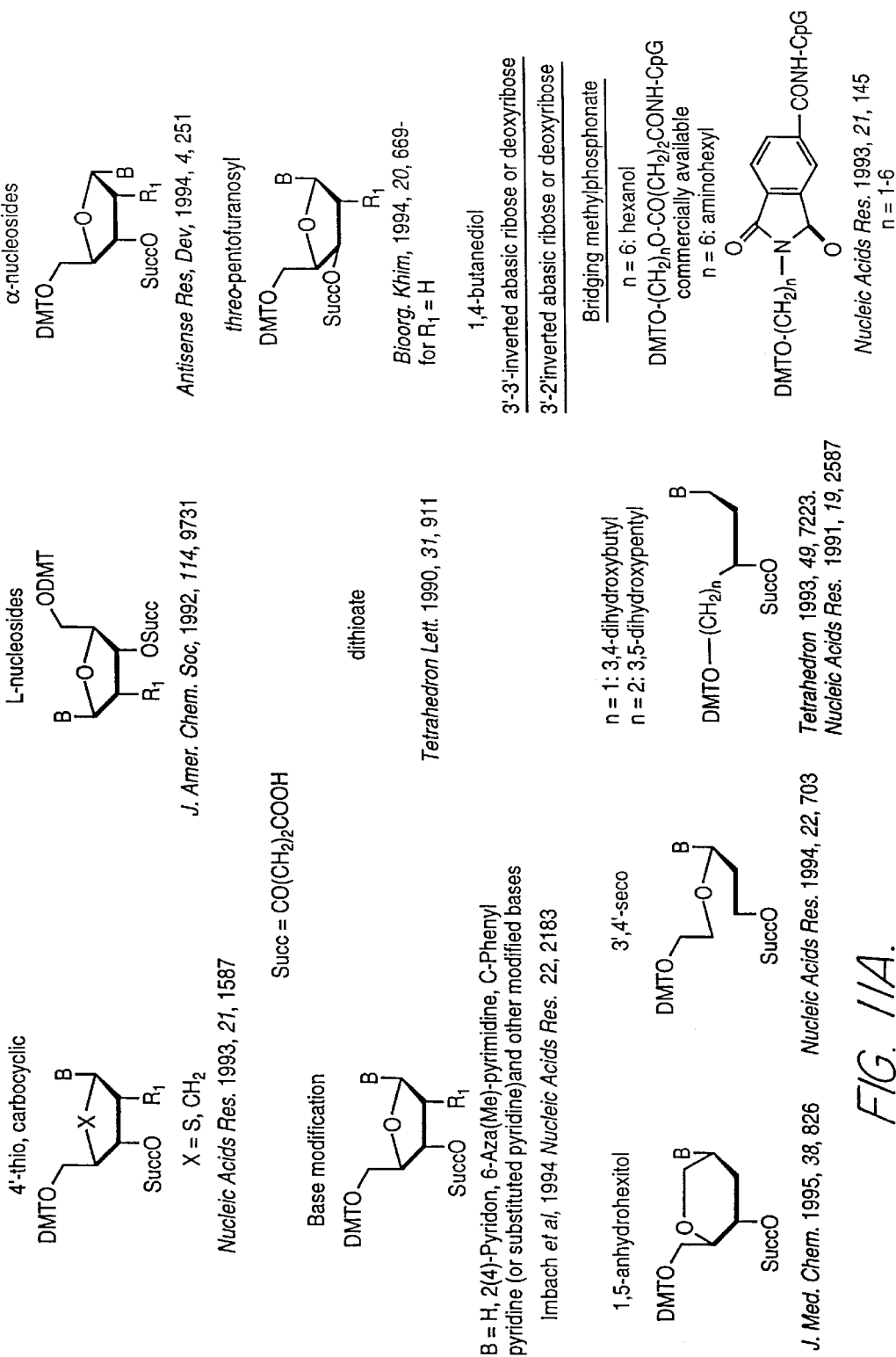
Figure 11B:
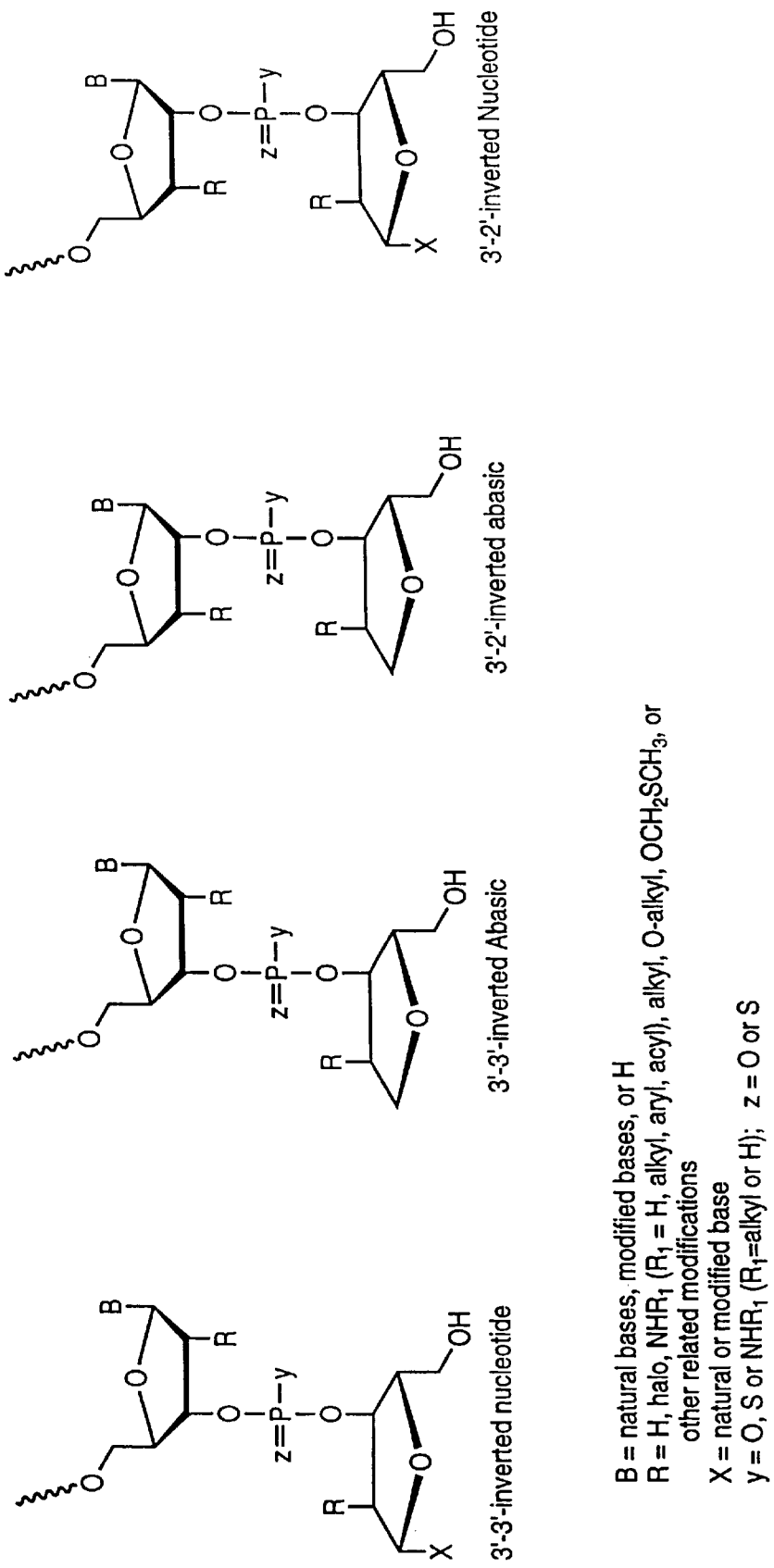

Reaction of compound 3, wherein B is H (see FIG. 17; compound 7), with compound 2 will result in a 3'-2'-inverted abasic linkage as shown in FIG. 11B (3'-2'-inverted abasic).

Refering to FIG. 17, compound 7 can be reacted with compound 2 in FIG. 13 to yield a 3'-2'-inverted abasic deoxyribose linkage as shown in FIG. 11B.

Alternatively, 7 (FIG. 17) can be reacted with a standard nucleoside phosphoramidite to yield a 3'-3'-inverted abasic deoxyribose linkage as shown in FIG. 11B.

Example 11

In vitro RNA Cleavage Activity of Ribozymes with 5'-Terminal Phosphorodithioate Modifications Radio-labeling of Ribozymes and Substrates. Substrates were 5'-end-labeled using T4 Polynucleotide Kinase and $\gamma$-$^{32}$P-ATP.

Ribozyme Activity Assay. Ribozymes and 5'-$^{32}$P-end-labeled substrate were heated separately in reaction buffer (50 mM Tris-HCl, pH 7.5; 10 mM $MgCl_2$) to 95° C. for 2 min, quenched on ice, and equilibrated to the final reaction temperature (37° C.) prior to starting the reactions. Reactions were carried out in enzyme excess, and were started by mixing 1 nM substrate with the indicated amounts of ribozyme (50 nM-1 μM) to a final volume of 50 μL. Aliquots of 5 μL were removed at 1, 5, 15, 30, 60 and 120 min, quenched in formamide loading buffer, and loaded onto 15% polyacrylamide/8 M Urea gels. The fraction of substrate and product present at each time point was determined by quantitation of scanned images from a Molecular Dynamics PhosphorImager. Ribozyme cleavage rates were calculated from plots of the fraction of substrate remaining vs time using a double exponential curve fit (Kaleidagraph, Synergy Software). The fast portion of the curve was generally 60–90% of the total reaction, so that observed cleavage rates ($k_{obs}$) were taken from fits of the first exponential.

Referring to FIG. 18, ribozymes with either one or two phosphorodithioate substitutions were capable of catalyzing efficient RNA clevage reactions. The results show that modification of ribozymes at the 5'-end do not significantly effect the activity of ribozymes.

Uses

The 5'- and/or 3'-substituted enzymatic nucleic acids of this invention can be used to form stable molecules with enhanced activity as discussed above for use in enzymatic cleavage of target RNA. Such nucleic acids can be formed enzymatically using triphosphate forms by standard procedure. Administration of such nucleic acids into cells is by standard methods. Their in vitro utility is as known in the art. See Sullivan et al., PCT WO 94/ 02595.

Diagnostic Uses

Enzymatic nucleic acids of this invention may be used as diagnostic tools to examine genetic drift and mutations within diseased cells or to detect the presence of target RNA in a cell. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNAs associated with disease condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

SEQUENCE LISTING (1) GENERAL INFORMATION:

(iii) NUMBER OF SEQUENCES:      8

(2) INFORMATION FOR SEQ ID NO:   1:

(i) SEQUENCE CHARACTERISTICS:
      (A) LENGTH:            11
      (B) TYPE:              nucleic acid
      (C) STRANDEDNESS:      single
      (D) TOPOLOGY:          linear (ix) FEATURE:
      (D) OTHER INFORMATION:   The letter "N" stands for
          any base.  "H" represents
          nucleotide C, A, or U.

(xi) SEQUENCE DESCRIPTION:  SEQ ID NO:  1:

NNNNUHNNNN N                                                                   11

(2) INFORMATION FOR SEQ ID NO:   2:

(i) SEQUENCE CHARACTERISTICS:
      (A) LENGTH:            28

```
            (B) TYPE:                nucleic acid
            (C) STRANDEDNESS:        single
            (D) TOPOLOGY:            linear (ix) FEATURE:
            (D) OTHER INFORMATION:  The letter "N" stands for
                any base.

(xi) SEQUENCE DESCRIPTION: SEQ ID NO: 2:

NNNNNCUGAN GAGNNNNNNC GAAANNNN                                          28

(2) INFORMATION FOR SEQ ID NO:    3:

(i) SEQUENCE CHARACTERISTICS:
            (A) LENGTH:             15
            (B) TYPE:                nucleic acid
            (C) STRANDEDNESS:        single
            (D) TOPOLOGY:            linear (ix) FEATURE:
            (D) OTHER INFORMATION:   The letter "N" stands for
                any base.  The leter "Y" stands
                for U or C.  The letter "H"
                stands for A, U, or C.

(xi) SEQUENCE DESCRIPTION: SEQ ID NO: 3:

NNNNNNNYNG HYNNN                                                        15

(2) INFORMATION FOR SEQ ID NO:    4:

(i) SEQUENCE CHARACTERISTICS:
            (A) LENGTH:             47
            (B) TYPE:                nucleic acid
            (C) STRANDEDNESS:        single
            (D) TOPOLOGY:            linear (ix) FEATURE:
            (D) OTHER INFORMATION:   The letter "N" stands for
                any base.  The letter "H"
                stands for A, U, or C.

(xi) SEQUENCE DESCRIPTION: SEQ ID NO: 4:

NNNNGAAGNN NNNNNNNNNA AAHANNNNNN NACAUUACNN NNNNNNN                     47

(2) INFORMATION FOR SEQ ID NO:    5:

(i) SEQUENCE CHARACTERISTICS:
            (A) LENGTH:             45
            (B) TYPE:                nucleic acid
            (C) STRANDEDNESS:        single
            (D) TOPOLOGY:            linear (ix) FEATURE:
            (D) OTHER INFORMATION:   The letter "N" stands for
                any base.

(xi) SEQUENCE DESCRIPTION: SEQ ID NO: 5:

CUCCACCUCC UCGCGGUNNN NNNNGGGCUA CUUCGGUAGG CUAAG                       45

(2) INFORMATION FOR SEQ ID NO:    6:

(i) SEQUENCE CHARACTERISTICS:
            (A) LENGTH:             176
            (B) TYPE:                nucleic acid
            (C) STRANDEDNESS:        single
            (D) TOPOLOGY:            linear (xi) SEQUENCE DESCRIPTION: SEQ ID NO: 6:

GGGAAAGCUU GCGAAGGGCG UCGUCGCCCC GAGCGGUAGU AAGCAGGGAA CUCACCUCCA       60
```

-continued

```
AUUUCAGUAC UGAAAUUGUC GUAGCAGUUG ACUACUGUUA UGUGAUUGGU AGAGGCUAAG        120

UGACGGUAUU GGCGUAAGUC AGUAUUGCAG CACAGCACAA GCCCGCUUGC GAGAAU           176

(2) INFORMATION FOR SEQ ID NO:    7:

(i) SEQUENCE CHARACTERISTICS:
        (A) LENGTH:              15
        (B) TYPE:                nucleic acid
        (C) STRANDEDNESS:        single
        (D) TOPOLOGY:            linear (xi) SEQUENCE DESCRIPTION:  SEQ ID NO:   7:

AGGGAAUAAU GGAGA                                                         15

(2) INFORMATION FOR SEQ ID NO:    8:

(i) SEQUENCE CHARACTERISTICS:
        (A) LENGTH:              36
        (B) TYPE:                nucleic acid
        (C) STRANDEDNESS:        single
        (D) TOPOLOGY:            linear (xi) SEQUENCE DESCRIPTION:  SEQ ID NO:   8:

UCUCCAUCUG AUGAGGCCGA AAGGCCGAAA AUCCCU                                  36
```

Other embodiments are within the following claims.

TABLE I

Characteristics of Ribozymes

Group I Introns

Size: ~150 to >1000 nucleotides.
Requires a U in the target sequence immediately 5' of the cleavage site.
Binds 4–6 nucleotides at 5' side of cleavage site.
Over 75 known members of this class. Found in *Tetrahymena thermophila* rRNA, fungal mitochondria, chloroplasts, phage T4, blue-green algae, and others.
RNase P RNA (M1 RNA)

Figure 2:
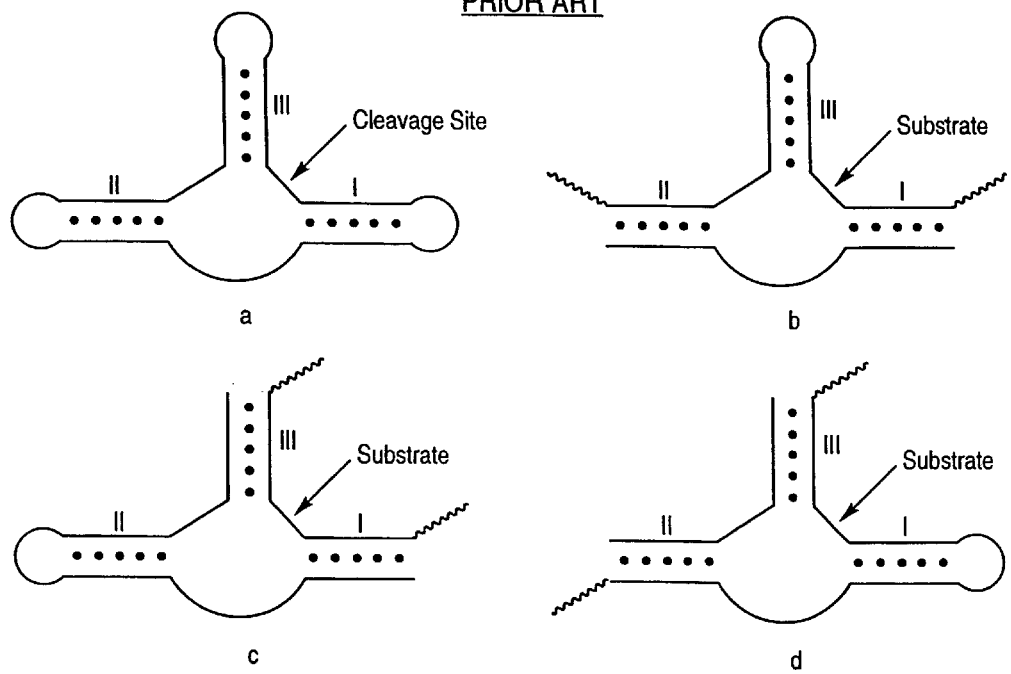

Size: ~290 to 400 nucleotides.
RNA portion of a ribonucleoprotein enzyme. Cleaves tRNA precursors to form mature tRNA.
Roughly 10 known members of this group all are bacterial in origin.
Hammerhead (HH) Ribozyme Size: ~13 to 40 nucleotides.
Requires the target sequence UH immediately 5' of the cleavage site.
Binds a variable number of nucleotides on both sides of the cleavage site.
14 known members of this class. Found in a number of plant pathogens (virusoids) that use RNA as the infectious agent (FIG. 1 and 2).
Hairpin (HP) Ribozyme Size: ~50 nucleotides.
Prefers the target sequence GUC immediately 3' of the cleavage site.
Binds 4–6 nucleotides at 5' side of the cleavage site and a variable number to the 3' side of the cleavage site.
Only 3 known member of this class. Found in three plant pathogen (satellite RNAs of the tobacco ringspot virus, arabis mosaic virus and chicory yellow mottle virus) which uses RNA as the infectious agent (FIG. 3).
Hepatitis Delta Virus (HDV) Ribozyme Size: 50–60 nucleotides (at present).
Sequence requirements not fully determined.
Binding sites and structural requirements not fully determined, although no sequences 5' of cleavage site are required.

TABLE I-continued

Characteristics of Ribozymes

Figure 4:
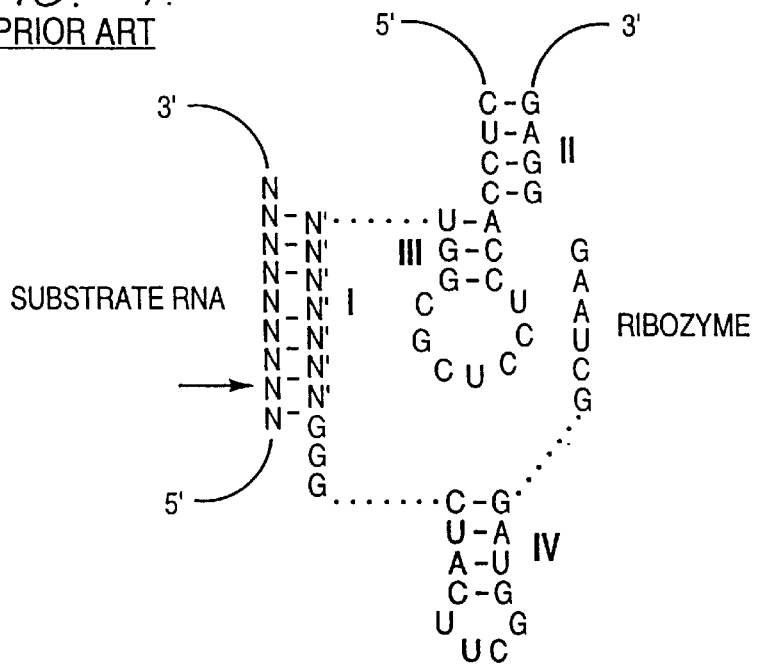

Only 1 known member of this class. Found in human HDV (FIG. 4).
Neurospora VS RNA (VS) Ribozyme Size: ~144 nucleotides (at present)
Cleavage of target RNAs recently demonstrated.
Sequence requirements not fully determined.
Binding sites and structural requirements not fully determined. Only 1 known member of this class. Found in Neurospora VS RNA (FIG. 5).

TABLE II

Hammerhead Ribozyme Modifications at the 5'-Terminus or Positions 2.1–2.7

| | Chemical Composition | | |
|---|---|---|---|
| Ribozyme | 5'-Terminus | Positions 2.1–2.7 | U4/U7 |
| Rz 1 | OH | 2'-ribose | 2'-$NH_2$ |
| Rz 2 | OH | 2'-deoxyribose | 2'-$NH_2$ |
| Rz 3 | OH | 2'-O—Me | 2'-$NH_2$ |
| Rz 4 | OH | 2'-O—Me, (2.3–2.7 P=S) | 2'-$NH_2$ |
| Rz 5 (inactive)* | OH | 2'-O—Me, (2.3–2.7 P=S) | 2'-$NH_2$ |
| Rz 6 | $NH_2$ | 2'-O—Me | 2'-$NH_2$ |
| Rz 7 (inactive) | $NH_2$ | 2'-O—Me | 2'-$NH_2$ |
| Rz 8 | $NH_2$ | 2'-O—Me | 2'-C—allyl/O—Me |
| Rz 9 (inactive) | $NH_2$ | 2'-O—Me | 2'-C—allyl/O—Me |
| Rz 10 | OH | 2'-O—Me, (2.3–2.7 P=S) | 2'-C—allyl/O—Me |
| Rz 11 (inactive) | OH | 2'-O—Me, (2.3–2.7 P=S) | 2'-C—allyl/O—Me |

*Catalytically inactive ribozyme cores were produced by substituting 2'-O—Me U at positions G5 and A 14.

TABLE III

Comparative Catalytic Activities for U4/U7-amino-Containing-Hammerhead Ribozymes

| Ribozyme | $k_{obs}$ (min$^{-1}$) [Rz] = 40 nM | $k_{obs}$ (min$^{-1}$) [Rz] = 500 nM* |
|---|---|---|
| Rz 1 | 0.128 ± 0.032 | 0.140 ± 0.015 |
| Rz 2 | 0.019 ± 0.002 | 0.023 ± 0.002 |
| Rz 3 | 0.163 ± 0.012 | 0.200 ± 0.015 |
| Rz 4 | 0.108 ± 0.001 | 0.150 ± 0.003 |
| Rz 6 | 0.131 ± 0.007 | 0.149 ± 0.007 |

*Neither U4-C—allyl containing ribozymes nor ribozymes containing inactivating nucleotide changes exhibited measurable activity under the standard conditions employed for these measurements. $k_{obs}$ is derived from two independent assays and is expressed as average ± range. Values in parentheses express the cleavage rate as a percentage of the control cleavage rate using Rz 3 at equivalent concentrations.

TABLE IV

Inhibition of Rat Smooth Cell Proliferation in Culture
Relative Proliferation Index
[Ribozyme] nM

| Ribozyme | 50 nM | 100 nM | 200 nM |
|---|---|---|---|
| Rz 1 | 83 ± 9 | 75 ± 12 | 57 ± 10 |
| Rz 2 | 104 ± 5 | 80 ± 6 | 58 ± 7 |
| Rz 3 | 103 ± 7 | 82 ± 13 | 57 ± 10 |
| Rz 4 | 82 ± 11 | 31 ± 11 | 24 ± 5 |
| Rz 5 | 83 ± 5 | 31 ± 8 | 38 ± 5 |
| Rz 6 | 88 ± 7 | 24 ± 7 | 18 ± 6 |
| Rz 7 | 104 ± 3 | 69 ± 13 | 40 ± 6 |
| Rz 8 | 106 ± 3 | 71 ± 9 | 47 ± 7 |
| Rz 9 | 103 ± 6 | 87 ± 7 | 56 ± 7 |
| Rz 10 | 79 ± 9 | 17 ± 5 | 26 ± 12 |
| Rz 11 | 93 ± 12 | 69 ± 11 | 32 ± 9 |

Values given represent the percentage of proliferating cell nuclei relative to stimulated lipid-treated cell controls. Mean values of at least 9 experimental points were used to obtain the relative proliferative index for each treatment protocol. Numbers in parentheses represent the standard deviation of the mean values. Unstimulated control values were 5 (±2)%. The percentage of proliferating nuclei in the serum stimulated control wells was 72 (±6)%.

TABLE V

RNA Synthesis Cycle (2.5 μmol Scale)

| Reagent | Equivalents | Amount | Wait Time* |
|---|---|---|---|
| Phosphoramidites | 6.5 | 163 μL | 2.5 |
| S-Ethyl Tetrazole | 23.8 | 238 μL | 2.5 |
| Acetic Anhydride | 100 | 233 μL | 5 sec |
| N-Methyl Imidazole | 186 | 233 μL | 5 sec |
| TCA | 83.2 | 1.73 mL | 21 sec |
| Iodine | 8.0 | 1.18 mL | 45 sec |
| Acetonitrile | NA | 6.67 mL | NA |

*Wait time does not include contact time during delivery.

TABLE VI

5'-Amino-5'-deoxynucleotide incorporation

| Experiment | Coupling of 5 | Coupling of 2'-O—Me—G | Desilylating Reagent | Crude AU | % FLP |
|---|---|---|---|---|---|
| 4298 | 600 s | 600 s | HF/TEA | 355.3 | 14.8 |
| 4298 | 600 s | 600 s | TBAF | 387.3 | 22.2 |
| 4523 | 600 s | 900 s | TBAF | 401.7 | 21.4 |
| 4545 | 600 s | 450 s | TBAF | 447.8 | 23.8 |
| 4649 | 300 s | 300 s | TBAF | 455.4 | 27.3 |

What is claimed is:

1. A nucleic acid molecule comprising a 5'-cap structure, a 3'-cap structure, or both a 5'- and a 3'-cap structure, wherein said 5'-cap structure is selected from the group consisting of 4',5'-methylene nucleotide; 1-(β-D-erythrofuranosyl) nucleotide; 1,3-diamino-2-propyl phosphate, 3-aminopropyl phosphate; 12-aminododecyl phosphate; hydroxypropyl phosphate; 1,5-anhydrohexitol nucleotide; L-nucleotide; threo-pentofuranosyl nucleotide; acyclic 3',4'-seco nucleotide; 3,5-dihydroxypentyl nucleotide; and 5'-mercapto moieties, and wherein said 3'-cap structure is selected from the group consisting of 1,5-anhydrohexitol nucleotide; L-nucleotide; threo-pentofuranosyl nucleotide; acyclic 3',4'-seco nucleotide; 3,5-dihydroxypentyl nucleotide; 3'-2'-inverted nucleotide moiety; 3'-2'-inverted abasic moiety; and 1,4-butanediol.

2. The nucleic acid molecule of claim 1, wherein said nucleic acid molecule is in an enzymatic nucleic acid molecule.

3. The nucleic acid molecule of claim 1, wherein said nucleic acid molecule is in an antisense nucleic acid molecule.

4. The nucleic acid molecule of claim 2, wherein said enzymatic nucleic acid molecule is in a hairpin, hepatitis delta virus, group I intron, VS RNA or RNase P RNA motif.

5. The nucleic acid molecule of claim 1, wherein said nucleic acid molecule comprises said 5'-cap structure.

6. The nucleic acid molecule of claim 1, wherein said nucleic acid molecule comprises said 3'-cap structure.

7. The nucleic acid molecule of claim 1, wherein said nucleic acid molecule comprises said 5'-cap structure and said 3'-cap structure.

8. The nucleic acid molecule of claim 1, wherein said 5'- and 3'-cap structures are different.

9. The nucleic acid molecule of claim 1, wherein said 5'- and 3'-cap structures are same.

10. The nucleic acid of claim 1, wherein said 3'-cap structure is a 3'-2' linked inverted nucleotide.

11. The nucleic acid of claim 1, wherein said 3'-cap structure is a 3'-2' linked inverted abasic moiety.

12. The nucleic acid of claim 1, wherein said 5'-cap structure is a 1,3-diamino-2propyl phosphate group.

13. The nucleic acid of claim 1, wherein said 5'-cap structure is a L-nucleotide.

14. The nucleic acid of claim 1, wherein said 5'-cap structure is a threo-pentafuranosyl group.

15. The nucleic acid of claim 1, wherein said 5'-cap structure is a 3,5-dihydroxypentyl nucleotide.

16. The nucleic acid of claim 1, wherein said 5'-cap structure is a 1-(β-D-erythrofuranosyl) nucleotide.

17. The nucleic acid of claim 1, wherein said 3'-cap structure is a L-nucleotide.

18. The nucleic acid of claim 1, wherein said 3'-cap structure is a 3,5-dihydroxypentyl nucleotide.

19. An isolated mammalian cell comprising the nucleic acid molecule of claim 1.

20. The mammalian cell of claim 19, wherein said mammalian cell is a human cell.

* * * * *